(12) United States Patent
De Both et al.

(10) Patent No.: US 6,563,026 B2
(45) Date of Patent: May 13, 2003

(54) HYBRID WINTER OILSEED RAPE AND METHODS FOR PRODUCING SAME

(75) Inventors: Greta De Both, Wetteren (BE); Marc De Beuckeleer, Zwijnaarde (BE)

(73) Assignee: Aventis CropScience N.V., Ghent (BE)

( * ) Notice: Subject to any disclaimer, the term of this patent is extended or adjusted under 35 U.S.C. 154(b) by 0 days.

(21) Appl. No.: 09/733,151

(22) Filed: Dec. 8, 2000

(65) Prior Publication Data

US 2001/0029620 A1 Oct. 11, 2001

Related U.S. Application Data

(63) Continuation-in-part of application No. 09/457,037, filed on Dec. 8, 1999.
(51) Int. Cl.[7] .............................. A01H 5/00; A01H 5/10; C12N 15/00; C12N 15/82; C12N 15/87
(52) U.S. Cl. ...................... 800/306; 435/419; 435/468; 435/199; 800/271; 800/274; 800/278; 800/288
(58) Field of Search ................................ 800/306, 278, 800/266, 267, 271, 274, 288; 435/468, 419, 199

(56) References Cited

U.S. PATENT DOCUMENTS 5,689,041 A * 11/1997 Mariani et al. ............. 800/205

FOREIGN PATENT DOCUMENTS

| EP | 0 270 615 B1 | 6/1988 |
| EP | 0412 911 A | 2/1991 |
| EP | 0 116 718 B2 | 5/1996 |
| EP | 0 344 029 B1 | 1/1997 |
| EP | 0757 102 A | 2/1997 |
| WO | WO 96/26283 | 8/1996 |

OTHER PUBLICATIONS de Vrics et al. (editiors), The Molecular Genetics of Homologous Recombination In Plants, 2000, Dev. Plant Genet Breed, vol. 6, pp. 47–58.*

"A Chimaeric Ribonuclease–Inhibitor Gene Restores Fertility to Male Sterile Plants" Mariani et al., Nature, vol. 357, Jun. 4, 1992, pp. 384–387.

"Induction of male sterility in plants by a chimaeric ribonuclease gene," Mariani et al., Nature, vol. 327, Oct. 25, 1990, pp. 737–741.

"Engineered fertility control in transgenic *Brassica napus* L.: Histochemical analysis of anther development," De Block et al., , Planta (1993), 189: pp. 218–225.

"Genetic transformation of Brassica," Poulsen, G.B., Plant Breeding 115, 1996, pp. 209–225.

"A combined used of microprojectile bombardment and DNA inbibition enhances transformation frequency of canola (*Brassica napus* L.)," Chen et al., Theor Appl Genet (1994), pp. 187–192.

"Transformation of *Brassica napus* and *Brassica oleracea* Using *Agrobacterium tumefaciens* and the Expression of the bar and neo Genes in the Transgenic Plants, " De Block et al., Plant Physiol. (1989), pp. 694–701.

* cited by examiner

Primary Examiner—David T. Fox
Assistant Examiner—David H Kruse
(74) Attorney, Agent, or Firm—Frommer Lawrence & Haug LLP

(57) ABSTRACT

This invention relates to transgenic winter oilseed rape (WOSR) plants, plant material and seeds, wherein harboring a specific transformation event. It pertains to winter oilseed rape plants, more particularly to a pair of winter oilseed rape plants, which is particularly suited for the production of hybrid seed. More specifically, one plant is wherein being male-sterile, due to the presence in its genome of a male sterility gene, while the other is wherein carrying a fertility-restorer gene, capable of preventing the activity of the male-sterility gene. The invention further provides a method for producing hybrid seed, a process for producing a transgenic WOSR plant oil or plant, and a method to identify a transgenic plant, cell or tissue. A kit for identifying the transgenic plants comparing the elite event of the present invention is also described. The WOSR plants of the invention combine the ability to form hybrid seeds with optimal overall agronomic performance, genetic stability and adaptability to different generic backgrounds.

10 Claims, 5 Drawing Sheets

HYBRID WINTER OILSEED RAPE AND METHODS FOR PRODUCING SAME

CROSS-REFERENCE TO RELATED APPLICATIONS

This patent application is a continuation-in-part of U.S. Ser. No. 09/457,037 filed Dec. 8, 1999.

STATEMENT IN SUPPORT OF FEDERALLY SPONSORED RESEARCH

Not applicable.

FIELD OF THE INVENTION

This invention pertains to winter oilseed rape (WOSR) plants, more particularly a pair of winter oilseed rape plants, which is particularly suited for the production of hybrid seed. More specifically, the one plant is wherein being male-sterile, due to the presence in its genome of a male-sterility gene, while the other is wherein carrying a fertility-restorer gene, capable of preventing the activity of the male-sterility gene. The pair WOSR plants of the invention combine the ability to form hybrid seed with optimal overall agronomic performance, genetic stability and adaptability to different genetic backgrounds.

All documents cited herein are hereby incorporated herein by reference.

BACKGROUND OF THE INVENTION

The phenotypic expression of a transgene in a plant is determined both by the structure of the gene itself and by its location in the plant genome. At the same time the presence of the transgene at different locations in the genome will influence the overall phenotype of the plant in different ways. The agronomically or industrially successful introduction of a commercially interesting trait in a plant by genetic manipulation can be a lengthy procedure dependent on different factors. The transformation and regeneration of genetically transformed plants are only the first in a series of selection steps that include extensive genetic characterization, breeding, and evaluation in field trials.

Oilseed rape (OSR) (*Brassica napus*, AACC, 2n=38) is a natural hybrid resulting from the interspecies hybridization between Cole (*Brassica oleracea*, CC, 2n=18) and Turnip (*Brassica campestris*, AA, 2n=20). Winter oilseed rape is sown during the last 10 days of August and the first ten days of September and harvested the following July, needing a temperate period for vernalization. The faster growing spring rapes are sown during late March and early April being harvested mid August to September. The main types of OSR grown at present are low and high erucic acid varieties. Double low (00) varieties contain low (typically less than 1%) levels of erucic acids (which humans find hard to digest), and low levels of glucosinolates (which makes the meal by-product indigestible for animals). Current uses for "00" varieties include oil for human consumption and high protein meal for animal feed. Industrial uses include feedstocks for pharmaceuticals and hydraulic oils. High erucic acid rape (HEAR) varieties are grown specifically for their erucic acid content—typically 50–60% of oil. The principal end use of HEAR is to produce erucamide, a "slip agent" used in polyethane manufacture. A small portion is used to produce behenyl alcohol, which is added to a waxy crude mineral oil to improve its flow.

Oilseed rape plants are bisexual and typically 60–70% self-pollinated. The production of hybrids and introduction of genetic variation as a basis for selection was traditionally dependent on the adaptation of natural occurring phenomena such as self-incompatibility and cytoplasmic male sterility. Artificial pollination control methods such as manual emasculation or the use of gametocides are not widely applied in OSR breeding due to their limited practicability and high cost respectively.

Transgenic methods have been developed for the production of male or female-sterile plants, which provide interesting alternatives to the traditional techniques.

EP 0,344,029 describes a system for obtaining nuclear male sterility whereby plants are transformed with a male-sterility gene, which comprises, for example a DNA encoding a barnase under the control of a tapetum specific promoter, PTA29, which when incorporated into a plant ensures selective destruction of tapetum cells. Transformation of tobacco and oilseed rape plants with such a chimeric gene resulted in plants in which pollen formation was completely prevented. Mariani et al. (1990) Nature 347:737–741.

To restore fertility in the progeny of a male-sterile plant, a system was developed whereby the male-sterile plant is crossed with a transgenic plant carrying a fertility-restorer gene, which when expressed is capable of inhibiting or preventing the activity of the male-sterility gene (U.S. Pat. No. 5,689,041; U.S. Pat. No. 5,792,929). Such a fertility-restorer gene is placed under the control of a promoter directing expression at least in the cells in which the male-sterility gene is expressed. Mariani et al. ((1992) Nature 357:384–387) demonstrated that the sterility encoded by the pTA29: barnase gene can be restored by the chimeric pTA29: barstar gene in oilseed rape.

Cytochemical and histochemical analysis of anther development of *B. napus* plants comprising the chimeric pTA29: barnase gene alone or with pTA29: barstar is described by De Block and De Brouwer ((1993) Planta 189:218–225).

Successful transformation of Brassica species has been obtained by a number of methods including Agrobacterium infection (as described for example in EP 0,116,718 and EP 0,270,882), microprojectile bombardment (as described for example by Chen et al. (1994) Theor. Appl. Genet. 88:187–192) and direct DNA uptake (as described for example by De Block et al. (1989) Plant Physiol. 914:694–701; and Poulsen (1996) Plant Breeding 115:209–225.

However, the foregoing documents fail to teach or suggest the present invention.

SUMMARY OF THE INVENTION

The present invention relates to a pair of WOSR plants, particularly suited for producing hybrid seed. More particularly, the present invention relates to a first transgenic WOSR plant, or seed, cells or tissues thereof, comprising, integrated into its genome, an expression cassette which comprises a male-sterility gene, and a second transgenic WOSR plant, or seed, cells or tissues thereof, comprising, integrated into its genome, an expression cassette which comprises a fertility restorer gene, and the hybrid seed obtained by the crossing of the first and second plant, which comprises the male-sterility gene and/or the fertility restorer gene integrated into its genome.

In one embodiment, the first WOSR plant or seed, cells or tissues thereof, comprises the expression cassette of pTHW107. In the preferred embodiment of the invention the first WOSR plant or seed, cells or tissues thereof comprise event MS-BN1.

In another embodiment of the invention, the second WOSR plant or seed, cells or tissues thereof, comprises the expression cassette of pTHW1118. In the preferred embodiment of the invention the WOSR plant or seed, cells or tissues thereof comprise event RF-BN1. In a particularly preferred embodiment of the invention the first WOSR plant comprises event MS-BN1 and the second WOSR plant comprises event RF-BN1 and the hybrid seed obtained therefrom comprises event MS-BN1 and/or RF-BN1.

The invention relates to transgenic WOSR seed, or a plant that can be grown from such seed, the genomic DNA of which is wherein one or both of the following characteristics:

a) the genomic DNA is capable of yielding at least two, preferably at least three, more preferably at least four, most preferably five of the sets of restriction fragments selected from the group of:
  i) one set of two EcoRI fragments, one with a length of between 2140 and 2450 bp, preferably of about 2266 bp, and one with a length of more than 14 kbp;
  ii) one set of two EcoRV fragments wherein one has a length of between 1159 and 1700 bp, preferably of about 1.4 kbp and the other has a length of more than 14 kbp;
  iii) one set of two HpaI fragments, one with a length of between 1986 and 2140 bp, preferably with a length of about 1990 bp, and one with a length of between 2140 and 2450 bp, preferably of about 2229 bp;
  iv) one set of three AflIII fragments, one with a length of between 514 and 805 bp, preferably with a length of about 522 bp, and one with a length of between 2140 and 2450 bp, preferably about 2250 bp, and one with a length of between 2450 and 2838 bp, preferably of about 2477 bp.;
  v) one set of two NdeI fragments, both with a length of between 5077 and 14057 bp, preferably one of about 6500 bp, and one with a length of about 10 kbp;
  wherein each of the restriction fragments is capable of hybridizing under standard stringency conditions, with the 3942 bp fragment comprising the PTA29-barnase sequence obtainable by HindIII digestion of the plasmid pTHW107 described herein; and/or b) the genomic DNA is capable of yielding at least two, preferably at least three, more preferably four of the sets of restriction fragments selected from the group of:
  i) one set of three BamHI fragments, wherein one has a length of between 805 and 1099 bp, preferably of about 814 bp, one has a length between 1700 and 1986 bp, preferably of about 1849 bp, one has a length between 2450 and 2838 bp, preferably of about 2607 bp, and one has a length between 5077 and 14057 bp, preferably of about 6500 bp;
  ii) one set of four EcoRI fragments, one with a length of between 805 and 1159 bp, preferably of about 1094 bp, one with a length between 1986 and 2450 bp, preferably of about 2149 bp, and two with a length of between 5077 and 14057 bp, preferably one of about 7000 bp, and one with a length of about 10 kbp;
  iii) one set of two EcoRV fragments wherein both have a length of between 5077 and 14057 bp, preferably one has a length of about 5.4 kbp and the other has a length of about 8 kbp;
  iv) one set of three HindIII fragments, wherein one has a length of between 1700 and 2140 bp, preferably of about 1969 bp, and two have a length between 2450 and 2838 bp, preferably one has a length of about 2565 bp, and one has a length of about 2635 bp;

wherein each of the restriction fragments is capable of hybridizing under standard stringency conditions, with the 2182 bp fragment comprising the PTA29-barstar sequence obtainable by HpaI digestion of the plasmid pTHW118 described herein.

The present invention relates to a the seed of a WOSR plant, or a plant which can be grown from such seed, or cells, or tissues thereof, the genomic DNA of which is wherein one or both of the following characteristics:

a) the genomic DNA is capable of yielding at least two, preferably at least three, for instance at least four, more preferably five of the sets of restriction fragments selected from the group described under a) above comprising the sets of restriction fragments described under a) i), ii), iii), iv), and v) above, whereby the selection can include any combination of i), ii), iii), iv), and v) described under a) above; and/or b) the genomic DNA is capable of yielding at least two, preferably at least three, most preferably four of the sets of restriction fragments selected from the group described under b) above comprising the sets of restriction fragments described under b) i), ii), iii) and iv) above, whereby the selection can include any combination of i), ii), iii) and iv) described under b) above.

The invention further relates to WOSR seed, or plants grown from such seed, the genomic DNA of which is wherein one or both of the following characteristics:

c) the genomic DNA can be used to amplify a DNA fragment of between 260 and 300 bp, preferably of about 280 bp, using a polymerase chain reaction with two primers having the nucleotide sequence of SEQ ID NO:12 and SEQ ID NO:19 respectively; and/or d) the genomic DNA can be used to amplify a DNA fragment of between 195 and 235 bp, preferably of about 215 bp, using a polymerase chain reaction with two primers having the nucleotide sequence of SEQ ID NO:23 and SEQ ID NO:41 respectively.

The invention further relates to WOSR seed, or plants grown from such seed, the genomic DNA of which is wherein the characteristics described under a) and c) above and/or the characteristics described under b) and d) above.

The present invention relates to the seed of a WOSR plant, or a plant that can be grown from such seed, the genomic DNA of which is wherein one or both of the following characteristics:

a) the genomic DNA is capable of yielding at least two, preferably at least three, more preferably at least four, most preferably five of the sets of restriction fragments selected from the group of:
  i) one set of two EcoRI fragments, one with a length of between 2140 and 2450 bp, preferably of about 2266 bp, and one with a length of more than 14 kbp.
  ii) one set of two EcoRV fragments wherein one has a length of between 1159 and 1700 bp, preferably of about 1.4 kbp and the other has a length of more than 14 kbp.
  iii) one set of two HpaI fragments, one with a length of between 1986 and 2140 bp, preferably with a length of about 1990 bp, and one with a length of between 2140 and 2450 bp, preferably of about 2229 bp.
  iv) one set of three AflIII fragments, one with a length of between 514 and 805 bp, preferably with a length of about 522 bp, one with a length of between 2140 and 2450 bp, preferably about 2250 bp, and one with a length of between 2450 and 2838 bp, preferably of about 2477 bp.

v) one set of two NdeI fragments, both with a length of between 5077 and 14057 bp, preferably one of about 6500 bp, and one with a length of about 10 kbp;

wherein each of the restriction fragments is capable of hybridizing under standard stringency conditions, with the 3942 bp fragment comprising the PTA29-barnase sequence obtainable by HindIII digestion of the plasmid pTHW107 described herein; and/or, c) the genomic DNA can be used to amplify a DNA fragment of between 260 and 300 bp, preferably of about 280 bp, using a polymerase chain reaction with two primers having the nucleotide sequence of SEQ ID NO:12 and SEQ ID NO:19 respectively.

The present invention relates to a the seed of a WOSR plant, preferably a male-sterile plant, or a plant which can be grown from such seed, or cells, or tissues thereof, the genomic DNA of which is wherein it is capable of yielding at least two, preferably at least three, more preferably five of the sets of restriction fragments selected from the group described above comprising the sets of restriction fragments described under i), ii), iii), iv), and v) above, whereby the selection can include any combination of i), ii), iii), iv), and v) described above.

The present invention further relates to the seed of a WOSR plant, or a plant grown from such seed, the genomic DNA of which is wherein one or both of the following characteristics:

b) the genomic DNA is capable of yielding at least two, preferably at least three, more preferably four of the restriction fragments or sets of restriction fragments selected from the group of.

i) one set of three BamHI fragments, wherein one has a length of between 805 and 1099 bp, preferably of about 814 bp, one has a length between 1700 and 1986 bp, preferably of about 1849 bp, one has a length between 2450 and 2838 bp, preferably of about 2607 bp, and one has a length between 5077 and 14057 bp, preferably of about 6500 bp;

ii) one set of four EcoRI fragments, one with a length of between 805 and 1159 bp, preferably of about 1094 bp, one with a length between 1986 and 2450 bp, preferably of about 2149 bp, and two with a length of between 5077 and 14057 bp, preferably one of about 7000 bp, and one with a length of about 10 kbp;

iii) one set of two EcoRV fragments wherein both have a length of between 5077 and 14057 bp, preferably one has a length of about 5.4 kbp and the other has a length of about 8 kbp;

iv) one set of three HindIII fragments, wherein one has a length of between 1700 and 2140 bp, preferably of about 1969 bp, and two have a length between 2450 and 2838 bp, preferably one has a length of about 2565 bp, and one has a length of about 2635 bp;

wherein each of the restriction fragments is capable of hybridizing under standard stringency conditions, with the 2182 bp fragment comprising the PTA29-barstar sequence obtainable by HpaI digestion of the plasmid pTHW118 described herein; and/or d) the genomic DNA can be used to amplify a DNA fragment of between 195 and 235 bp, preferably of about 215 bp, using a polymerase chain reaction with two primers having the nucleotide sequence of SEQ ID NO:23 and SEQ ID NO:41 respectively.

The present invention relates to the seed of a WOSR plant, preferably a fertility restorer plant, or a plant which can be grown from such seed, or cells, or tissues thereof, the genomic DNA of which is capable of yielding at least two, preferably at least three, most preferably four of the sets of restriction fragments selected from the group described above comprising the sets of restriction fragments described under b) i), ii), iii) and iv) above, whereby the selection can include any combination of i), ii), iii) and iv) described above.

The present invention relates to transgenic WOSR plants, cells, tissues or seeds that preferably contain both of the characteristics described under b) and/or d) above, respectively.

The invention further relates to transgenic, preferably hybrid fertility restored WOSR plants, cells, tissues or seeds obtained from the crossing of the male-sterile plant with the fertility restorer plant of the invention wherein the respective characteristics described above, whereby the fertility restored plants, cells tissues or seeds are wherein both the molecular characteristics of the male-sterile and those of the fertility restorer WOSR plant described above. The invention further relates to transgenic, preferably hybrid WOSR plants, cells, tissues or seeds obtained from the crossing of the male-sterile plant with the fertility restorer plant of the invention wherein the molecular characteristics described above, whereby the hybrid plants, cells tissues or seeds are wherein the molecular characteristics of the fertility restorer WOSR plant described above.

The invention also relates to the seed deposited at the ATCC under accession number PTA-730, a plant which is grown from this seed, and cells or tissues from a plant grown from this seed. The invention further relates to plants obtainable by propagation of, and/or breeding with a WOSR plant grown from the seed deposited at the ATCC under accession number PTA-730.

The invention further relates to a process for producing hybrid WOSR seed, which comprises, crossing the male-sterile WOSR plant of the present invention with the fertility-restorer WOSR plant of the invention.

The invention further relates to a WOSR plant, plant cell, plant tissue or seed, which comprises a recombinant DNA comprising at least one transgene, integrated into a part of the chromosomal DNA wherein the sequence of SEQ ID NO:22 and/or a recombinant DNA comprising at least one transgene, integrated into a part of the chromosomal DNA wherein the sequence of SEQ ID NO:34.

The invention further provides a process for producing a transgenic cell of a WOSR plant or a plant obtained therefrom, which comprises inserting a recombinant DNA molecule into a part of the chromosomal DNA of an WOSR cell wherein the sequence of SEQ ID NO:22 and, optionally, regenerating a WOSR plant from the transformed WOSR cell.

The invention further provides a process for producing a transgenic cell of a WOSR plant or a plant obtained therefrom, which comprises inserting a recombinant DNA molecule into a part of the chromosomal DNA of an WOSR cell wherein the sequence of SEQ ID NO:34 and, optionally, regenerating a WOSR plant from the transformed WOSR cell.

The invention further relates to a method for identifying a transgenic plant, or cells or tissues thereof, comprising the elite event MS-BN1 of the invention, which method comprises establishing one or both of the following characteristics of the genomic DNA of the transgenic plant, or its cells or tissues:

a) the genomic DNA is capable of yielding at least two, preferably at least three, more preferably at least four, most preferably five of the sets of restriction fragments selected from the group of:
  i) one set of two EcoRI fragments, one with a length of between 2140 and 2450 bp, preferably of about 2266 bp, and one with a length of more than 14kbp;
  ii) one set of two EcoRV fragments wherein one has a length of between 1159 and 1700 bp, preferably of about 1.4 kbp and the other has a length of more than 14 kbp;
  iii) one set of two HpaI fragments, one with a length of between 1986 and 2140 bp, preferably with a length of about 1990 bp, and one with a length of between 2140 and 2450 bp, preferably of about 2229 bp;
  iv) one set of three AflIII fragments, one with a length of between 514 and 805 bp, preferably with a length of about 522 bp, one with a length of between 2140 and 2450 bp, preferably about 2250 bp, and one with a length of between 2450 and 2838 bp, preferably of about 2477 bp; and
  v) one set of two NdeI fragments, both with a length of between 5077 and 14057 bp, preferably one of about 6500 bp, and one with a length of about 10 kbp;
  wherein each of the restriction fragments is capable of hybridizing under standard stringency conditions, with the 3942 bp fragment comprising the PTA29-barnase sequence obtainable by HindIII digestion of the plasmid pTHW107 described herein; and/or
  c) the genomic DNA can be used to amplify a DNA fragment of between 260 and 300 bp, preferably of about 280 bp, according to the PCR Identification Protocol described herein with two primers identifying the elite event having the nucleotide sequence of SEQ ID NO:12 and SEQ ID NO:19 respectively.

The invention further relates to a method for identifying a transgenic plant, or cells or tissues thereof, comprising the elite event RF-BN1 of the invention, which method comprises establishing one or both of the following characteristics of the genomic DNA of the transgenic plant, or its cells or tissues:
  b) the genomic DNA is capable of yielding at least two, preferably at least three, more preferably four of the restriction fragments or sets of restriction fragments selected from the group of:
    i) one set of three BamHI fragments, wherein one has a length of between 805 and 1099 bp, preferably of about 814 bp, one has a length between 1700 and 1986 bp, preferably of about 1849 bp, one has a length between 2450 and 2838 bp, preferably of about 2607 bp, and one has a length between 5077 and 14057 bp, preferably of about 6500 bp;
    ii) one set of four EcoRI fragments, one with a length of between 805 and 1159 bp, preferably of about 1094 bp, one with a length between 1986 and 2450 bp, preferably of about 2149 bp, and two with a length of between 5077 and 14057 bp, preferably one of about 7000 bp, and one with a length of about 10 kbp;
    iii) one set of two EcoRV fragments wherein both have a length of between 5077 and 14057 bp, preferably one has a length of about 5.4 kbp and the other has a length of about 8 kbp;
    iv) one set of three HindIII fragments, wherein one has a length of between 1700 and 2140 bp, preferably of about 1969 bp, and two have a length between 2450 and 2838 bp, preferably one has a length of about 2565 bp, and one has a length of about 2635 bp;
  wherein each of the restriction fragments is capable of hybridizing under standard stringency conditions, with the 2182 bp fragment comprising the PTA29-barstar sequence obtainable by HpaI digestion of the plasmid pTHW118 described herein, and/or
  d) the genomic DNA can be used to amplify a DNA fragment of between 195 and 235 bp, preferably of about 215 bp, using the PCR identification protocol described herein with two primers identifying the elite event having the nucleotide sequence of SEQ ID NO:23 and SEQ ID NO:41 respectively.

The invention also relates to a kit for identifying the plants comprising elite event MS-BN1 of the present invention, said kit comprising the PCR probes having the nucleotide sequence of SEQ ID NO:12 and SEQ ID NO:19.

The invention further relates to a kit for identifying the plants comprising elite event RF-BN1 of the present invention, said kit comprising the PCR probes having the nucleotide sequence of SEQ ID NO:23 and SEQ ID NO:41.

The invention also relates to a kit for identifying elite event MS-BN1 and/or RF-BN1 in biological samples, which kit comprises at least one specific primer or probe having a sequence which corresponds (or is complementary to) a sequence having between 80% and 100% sequence identity with a specific region of MS-BN1 and/or at least one specific primer or probe having a sequence which corresponds (or is complementary to) a sequence having between 80% and 100% sequence identity with a specific region of RF-BN1. Preferably the sequence of the probe corresponds to a specific region comprising part of the 5' or 3' flanking region of MS-BN1 and/or RF-BN1. Most preferably the specific probe has (or is complementary to) a sequence having between 80% and 100% sequence identity to the plant DNA sequence within SEQ ID NO:36 or SEQ ID NO:38 for MS-BN1 or to the plant DNA sequence within SEQ ID NO:39 or SEQ ID NO:40 for RF-BN1.

Preferably the kit of the invention comprises, in addition to a primer which specifically recognizes the 5' or 3' flanking region of MS-BN1 and/or RF-BN1, a second primer which specifically recognizes a sequence within the foreign DNA of MS-BN1 and/or RF-BN1, for use in a PCR identification protocol. Preferably, the kit of the invention comprises two (or more) specific primers, one of which recognizes a sequence within the 3'flanking region of MS-BN1 and/or RF-BN1, most preferably a sequence within the plant DNA region of SEQ ID NO:36 or SEQ ID NO:38 for MS-BN1 or to the plant DNA sequence of SEQ ID NO:39 or SEQ ID NO:40 for RF-BN1, and another which recognizes a sequence within the foreign DNA of MS-BN1 and/or RF-BN1 respectively. Especially preferably, the primer recognizing the plant DNA sequence within 5' flanking region of MS-BN1 comprises the nucleotide sequence of SEQ ID NO:19. Particularly, the primer recognizing the plant DNA sequence within 5'flanking region of MS-BN1 comprises the nucleotide sequence of SEQ ID NO:19 and the primer recognizing the foreign DNA of MS-BN1 comprises the nucleotide sequence of SEQ ID NO:12 described herein. Especially preferably, the primer recognizing the plant DNA sequence within 5'flanking region of RF-BN1 comprises the nucleotide sequence of SEQ ID NO:41. Particularly, the primer recognizing the plant DNA sequence within 5'flanking region of MS-BN1 comprises the nucleotide sequence of SEQ ID NO:41 and the primer recognizing the foreign DNA of RF-BN1 comprises the nucleotide sequence of SEQ ID NO:23 described herein.

The methods and kits encompassed by the present invention can be used for different purposes such as, but not limited to the following: to identify MS-BN1 and/or RF-BN1 in plants, plant material or in products such as, but not limited to food or feed products (fresh or processed) comprising or derived from plant material; additionally or alternatively, the methods and kits of the present invention can be used to identify transgenic plant material for purposes of segregation between transgenic and non-transgenic material; additionally or alternatively, the methods and kits of the present invention can be used to determine the quality (i.e. percentage pure material) of plant material comprising MS-BN1 and/or RF-BN1.

It will be understood that particular embodiments of the invention are described by the dependent claims cited herein.

BRIEF DESCRIPTION OF THE DRAWINGS

The following detailed description, given by way of example, but not intended to limit the invention to specific embodiments described, may be understood in conjunction with the accompanying Figures, incorporated herein by reference, in which.

DETAILED DESCRIPTION OF THE INVENTION

Figure 1:
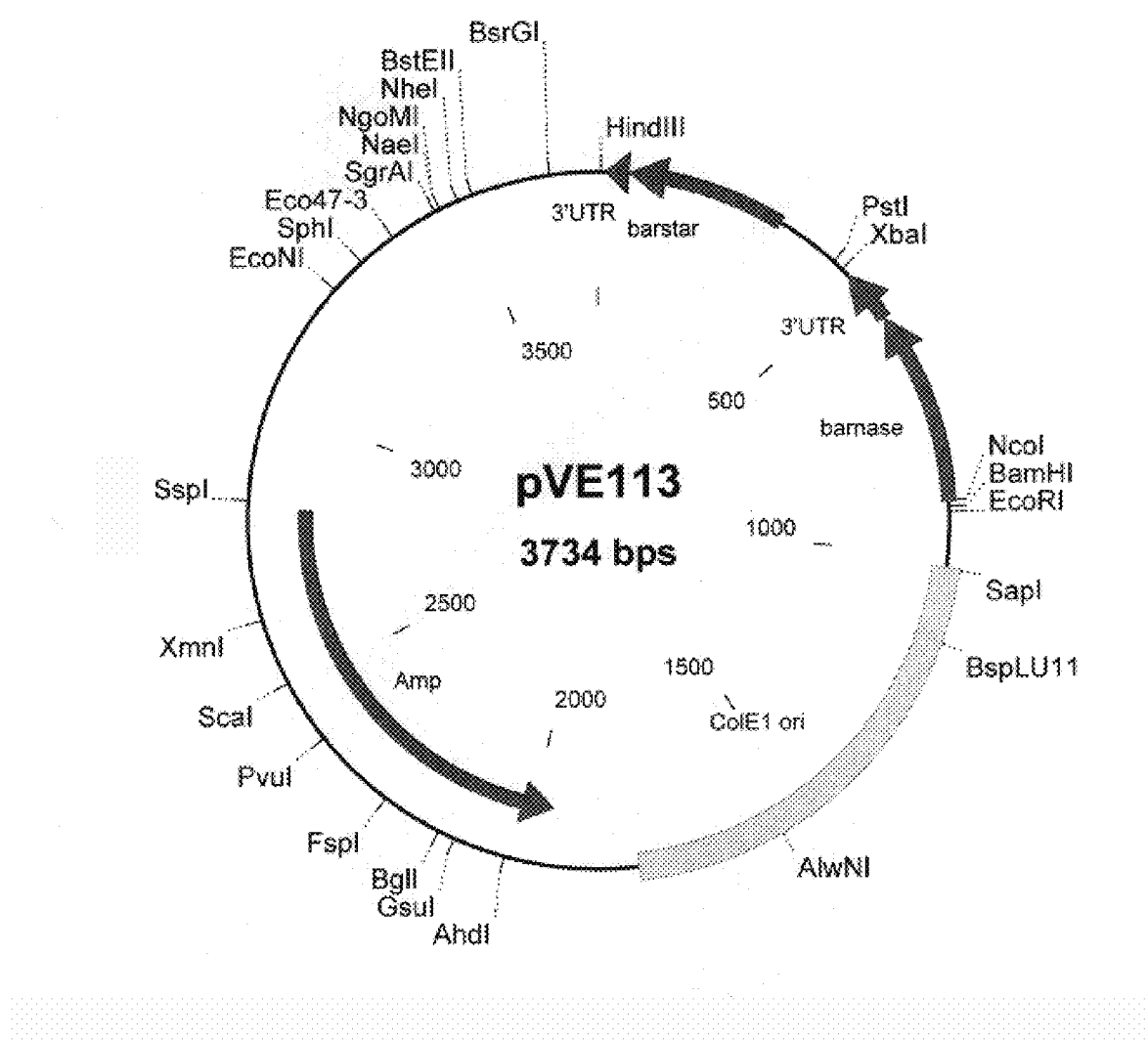
FIG. 1 depicts a plasmid map of pVE113.

The term "gene" as used herein refers to any DNA sequence comprising several operably linked DNA fragments such as a promoter and a 5' untranslated region (the 5'UTR), which together form the promoter region, a coding region (which may or may not code for a protein), and an untranslated 3' region (3'UTR) comprising a polyadenylation site. Typically in plant cells, the 5'UTR, the coding region and the 3'UTR are transcribed into a RNA which, in the case of a protein encoding gene, is translated into the protein. A gene may include additional DNA fragments such as, for example, introns. As used herein, a genetic locus is the position of a given gene in the genome of a plant.

The term "chimeric" when referring to a gene or DNA sequence is used to indicate that the gene or DNA sequence comprises at least two functionally relevant DNA fragments (such as promoter, 5'UTR, coding region, 3'UTR, intron) that are not naturally associated with each other and originate, for example, from different sources. "Foreign" referring to a gene or a DNA sequence with respect to a plant species is used to indicate that the gene or DNA sequence is not naturally found in that plant species, or is not naturally found in that genetic locus in that plant species. The term "foreign DNA" will be used herein to refer to a DNA sequence as it has incorporated into the genome of a plant as a result of transformation. The "transforming DNA" as used herein refers to a recombinant DNA molecule used for transformation. The transforming DNA usually comprises at least one "gene of interest" (e.g. a chimeric gene) which is capable of conferring one or more specific characteristics to the transformed plant. The term "recombinant DNA molecule" is used to exemplify and thus can include an isolated nucleic acid molecule which can be DNA and which can be obtained through recombinant or other procedures.

As used herein the term "transgene" refers to a gene of interest as incorporated in the genome of a plant. A "transgenic plant" refers to a plant comprising at least one transgene in the genome of all of its cells.

The foreign DNA present in the plants of the present invention will preferably comprise two genes of interest, more specifically, either a male-sterility gene and a herbicide resistance gene or a fertility restorer gene and a herbicide resistance gene.

A "male-sterility gene" as used herein refers to a gene that upon expression in the plant renders the plant incapable of producing fertile, viable pollen. An example of a male sterility gene is a gene comprising a DNA sequence encoding barnase, under the control of a promoter directing expression in tapetum cells. More specifically, according to the present invention the male-sterility gene is "TA29-barnase" as described herein.

A "fertility restorer gene" as used herein refers to a gene that upon expression in a plant comprising a male-sterility gene, is capable of preventing phenotypic expression of the male-sterility gene, restoring fertility in the plant. More specifically the fertility restorer gene will comprise a DNA encoding a protein or polypeptide capable of preventing phenotypic expression of the male-sterility gene, under the control of a promoter directing expression in at least the cells in which the male-sterility DNA is expressed. More specifically, according to the present invention, the fertility restorer gene is "TA29-barstar" as described herein.

The incorporation of a recombinant DNA molecule in the plant genome typically results from transformation of a cell or tissue (or from another genetic manipulation). The particular site of incorporation is either due to chance or is at a predetermined location (if a process of targeted integration is used).

The foreign DNA can be wherein the location and the configuration at the site of incorporation of the recombinant DNA molecule in the plant genome. The site in the plant genome where a recombinant DNA has been inserted is also referred to as the "insertion site" or "target site". Insertion of the transgene into the plant genome can be associated with a deletion of plant DNA, referred to as "target site deletion". A "flanking region" or "flanking" sequence as used herein refers to a sequence of at least 20 bp, preferably at least 50 bp, and up to 5000 bp of the plant genome which is located either immediately upstream of and contiguous with or immediately downstream of and contiguous with the foreign DNA. Transformation procedures leading to random integration of the foreign DNA will result in transformants with different flanking regions, which are characteristic and unique for each transformant. When the transgene is introduced into a plant through traditional crossing, its insertion site in the plant genome, or its flanking regions will generally not be changed. An "insertion region" as used herein refers to the region corresponding to the region of at least 40 bp, preferably at least 100 bp, and up to more than 10000 bp, encompassed by the upstream and the downstream flanking regions of a transgene in the (untransformed) plant genome and including the insertion site (and possible target site deletion). Taking into consideration minor differences due to mutations within a species, an insertion region will retain at least 85%, preferably 90%, more preferably 95%, and most preferably 100% sequence identity with the sequence comprising the upstream and downstream flanking regions of the foreign DNA in a given plant of that species.

Expression of a gene of interest refers to the fact that the gene confers on the plant one or more phenotypic traits (e.g. herbicide tolerance) that were intended to be conferred by the introduction of the recombinant DNA molecule—the transforming DNA—used during transformation (on the basis of the structure and function of part or all of the gene(s) of interest).

An "event" is defined as a (artificial) genetic locus that, as a result of genetic manipulation, carries a foreign DNA comprising at least one copy of the gene(s) of interest. The typical allelic states of an event are the presence or absence of the foreign DNA. As used herein an "MS" event and an "RF" event will refer to events carrying the "TA29-barnase" and "TA29-barstar" transgenes respectively. An event is characterized phenotypically by the expression of one or more transgene. At the genetic level, an event is part of the genetic makeup of a plant. At the molecular level, an event is wherein the restriction map (e.g. as determined by Southern blotting) and/or by the upstream and/or downstream flanking sequences of the transgene, and/or the molecular configuration of the transgene. Usually transformation of a plant with a transforming DNA comprising at least one gene of interest leads to a multitude of events, each of which is unique.

An "elite event", as used herein, is an event which is selected from a group of events, obtained by transformation with the same transforming DNA or by back-crossing with plants obtained by such transformation, based on the expression and stability of the transgene and its compatibility with optimal agronomic characteristics of the plant comprising it. Thus the criteria for elite event selection are one or more, preferably two or more, advantageously all of the following:
  a) That the presence of the transgene does not compromise other desired characteristics of the plant, such as those relating to agronomic performance or commercial value;
  b) That the event is wherein a well defined molecular configuration which is stably inherited and for which appropriate diagnostic tools for identity control can be developed;
  c) That the gene(s) of interest in the transgene show(s) a correct, appropriate and stable spatial and temporal phenotypic expression, both in heterozygous (or hemizygous) and homozygous condition of the event, at a commercially acceptable level in a range of environmental conditions in which the plants carrying the event are likely to be exposed in normal agronomic use;

It is preferred that the foreign DNA is associated with a position in the plant genome that allows introgression into desired commercial genetic backgrounds.

The status of an event as an elite event is confirmed by introgression of the elite event in different relevant genetic backgrounds and observing compliance with one, two or all of the criteria e.g. a), b) and c) above.

Additionally, for the transgenes encoding male sterility and fertility restoration described herein, selection of the elite events will also be determined on the compatibility between these events, more specifically that the progeny resulting from a cross between a plant carrying a male-sterility event and a plant carrying a fertility restorer event, in which both events are present have the following characteristics:
  a) adequate phenotypic expression of the fertility restored phenotype, i.e. male fertility; and
  b) phenotypic expression at a commercially acceptable level in a range of environmental conditions in which plants carrying the two events are likely to be exposed in normal agronomic use.

An "elite event" thus refers to a genetic locus comprising a transgene, which answers to the above-described criteria. A plant, plant material or progeny such as seeds can comprise one or more elite events in its genome.

The "diagnostic tools" developed to identify an elite event or the plant or plant material comprising an elite event, are based on the specific genomic characteristics of the elite event, such as, a specific restriction map of the genomic region comprising the foreign DNA and/or the sequence of the flanking region(s) of the transgene. A "restriction map" as used herein refers to a set of Southern blot patterns obtained after cleaving plant genomic DNA with a particular restriction enzyme, or set of restriction enzymes and hybridization with a probe sharing sequence similarity with the transgene under standard stringency conditions. Standard stringency conditions as used herein refers to the conditions for hybridization described herein or to the conventional hybridizing conditions as described by Sambrook et al. (1989) (Molecular Cloning: A Laboratory Manual, Second Edition, Cold Spring Harbor Laboratory Press, NY) which for instance can comprise the following steps: 1) immobilizing plant genomic DNA fragments on a filter, 2) prehybridizing the filter for 1 to 2 hours at 42° C. in 50% formamide, 5×SSPE, 2×Denhardt's reagent and 0.1% SDS, or for 1 to 2 hours at 68° C. in 6×SSC, 2×Denhardt's reagent and 0.1% SDS, 3) adding the hybridization probe which has been labeled, 4) incubating for 16 to 24 hours, 5) washing the filter for 20 min. at room temperature in 1×SSC, 0.1%SDS, 6) washing the filter three times for 20 min. each at 68° C. in 0.2×SSC, 0.1%SDS, and 7) exposing the filter for 24 to 48 hours to X-ray film at −70° C. with an intensifying screen.

Due to the (endogenous) restriction sites present in a plant genome prior to incorporation of the foreign DNA, insertion of a foreign DNA will alter the specific restriction map of that genome. Thus, a particular transformant or progeny derived thereof can be identified by one or more specific restriction patterns. The conditions for determining the restriction map of an event are laid out in a "restriction map identification protocol". Alternatively, once one or both of the flanking regions of the transgene have been sequenced, PCR-probes can be developed which specifically recognize this (these) sequence(s) in a "PCR identification protocol".

Plants or plant material comprising an elite event can be identified by testing according to the PCR identification protocol using these specific primers.

As used in herein, a "biological sample" is a sample of a plant, plant material or products comprising plant material. The term "plant" is intended to encompass WOSR (*B. napus*) plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts. "Plant material", as used herein refers to material which is obtained or derived from a plant. Products comprising plant material relate to food, feed or other products which are produced using plant material or can be contaminated by plant material. It is understood that, in the context of the present invention, such biological samples are preferably tested for the presence of nucleic acids specific for MS-BN1 and/or RF-BN1, implying the presence of nucleic acids in the samples. Thus the methods referred to herein for identifying elite event MS-BN1 and/or RF-BN1 in biological samples, preferably relate to the identification in biological samples of nucleic acids which comprise the elite event.

A "kit" as used herein refers to a set of reagents for the purpose of performing the method of the invention, more particularly, the identification of the elite event MS-BN1 and/or RF-BN1 in biological samples. More particularly, a preferred embodiment of the kit of the invention comprises at least one or two specific primers, as described above. Optionally, the kit can further comprise any other reagent described herein in the PCR identification protocol. Alternatively, according to another embodiment of this invention, the kit can comprise a specific probe, as described above, which specifically hybridizes with nucleic acid of biological samples to identify the presence of MS-BN1 and/or RF-BN1 therein. Optionally, the kit can further comprise any other reagent (such as but not limited to hybridizing buffer, label) for identification of MS-BN1 and/or RF-BN1 in biological samples, using the specific probe.

The kit of the invention can be used, and its components can be specifically adjusted, for purposes of quality control (e.g., purity of seed lots), detection of the elite event in plant material or material comprising or derived from plant material, such as but not limited to food or feed products.

The present invention relates to the development of a set of elite events in WOSR, MS-BN1 and RF-BN1, to the plants comprising these events, the progeny obtained from the crossing of these plants and to the plant cells, or plant material derived from these events. Plants comprising elite event MS-BN1 were obtained through transformation with pTHW107 as described in example 1. Plants comprising elite event RF-BN1 were obtained through transformation with pTHW118, also described in Example 1.

The recombinant DNA molecule used for generation of elite event MS-BN1 comprises a DNA sequence encoding a barnase molecule, under the control of a promoter directing expression selectively in tapetum cells (termed "TA29-barnase"). The TA29 promoter has a "tapetum selective" expression pattern in OSR. De Block and Debrouwer (1993) Planta 189:218–225. The expression of the TA29-barnase gene in WOSR plants results in destruction of the tapetum rendering the plants male-sterile (Mariani et al, 1990, above). The recombinant DNA molecule used for generation of elite event RF-BN1 comprises a DNA sequence encoding a barstar molecule, wherein the under the control of a tapetum specific promoter (termed "PTA29-barstar"). The expression of the TA29-barstar gene in WOSR plants will, in the presence of a "TA29-barnase" gene in the plant prevent the activity of barnase in the tapetum cells of the plant, preventing the destruction of the tapetum and thus restoring fertility in these plants (Mariani et al. 1992, above).

The recombinant DNAs used for the generation of elite event MS-BN1 and RF-BN1 both additionally comprise a DNA sequence encoding the enzyme phosphinothricin acetyl transferase and the 35S promoter of Cauliflower Mosaic Virus, wherein the sequence encoding phosphinothricin acetyl transferase is under the control of the 35S promoter (termed "35S-bar"). The 35S promoter has a "constitutive" expression pattern in OSR, which means that it is significantly expressed in most cell types, during most of the plant life cycle. The expression of the 35S-bar gene in OSR plants confers resistance to herbicidal compounds phosphinothricin or bialaphos or glufosinate, or more generally, glutamine synthetase inhibitors, or salts or optical isomers thereof.

WOSR Plants or plant material comprising MS-BN1 can be identified according to the restriction map identification protocol described for MS-BN1 in Example 5 herein. Briefly, WOSR genomic DNA is digested with a selection (preferably two to five) of the following restriction enzymes: EcoRI, EcoRV, NdeI, HpaI, AflIII, is then transferred to nylon membranes and hybridized with the 3942 bp HindIII fragment of plasmid pTHW107 (or of the T-DNA comprised therein). It is then determined for each restriction enzyme used whether the following fragments can be identified:

EcoRI: one fragment of between 2140 and 2450 bp, preferably of about 2266 bp, and one fragment of more than 14 kbp;

EcoRV: one fragment of between 1159 and 1700 bp, preferably of about 1,4 kbp and one fragment of more than 14 kbp;

HpaI: one fragment of between 1986 and 2140 bp, preferably of about 1990 bp, and one fragment of between 2140 and 2450 bp, preferably of about 2229 bp;

AflIII: one fragment of between 514 and 805 bp, preferably of about 522 bp, one fragment of between 2140 and 2450 bp, preferably of about 2250 bp, and one fragment of between 2450 and 2838 bp, preferably of about 2477 bp; and NdeI: two fragments with a length of between 5077 and 14057 bp, preferably one of about 6500 bp, and one with a length of about 10 kbp.

The lengths of the DNA fragments are determined by comparison with a set of DNA fragments of known length, particularly the PstI fragments of phage lambda DNA. A fragment of more than 14 kbp is estimated to have a length between 14 kbp and 40 kbp, when extraction of the DNA occurs according to the method of Dellaporta et al. (1983) Plant Mol. Biol. Rep. 3: 9–21.

If the plant material after digestion with at least two, preferably at least three, particularly with at least four, more particularly with all of these restriction enzymes, yields DNA fragments with the same length as those described above, the WOSR plant is determined to harbor elite event MS-BN1.

Plants or plant material comprising MS-BN1 can also be identified according to the PCR identification protocol described for MS-BN1 in Example 5 herein. Briefly, WOSR genomic DNA is amplified by PCR using a primer which specifically recognizes a flanking sequence of MS-BN1, preferably recognizing the 5' or 3' flanking sequence of MS-BN1 described herein, particularly the primer with the sequence of SEQ ID NO:19, and a primer which recognizes a sequence in the transgene, particularly the primer with the sequence of SEQ ID NO:12. Endogenous WOSR primers are used as controls. If the plant material yields a fragment of between 260 and 300 bp, preferably of about 280 bp, the WOSR plant is determined to harbor elite event MS-BN1.

Plants harboring MS-BN1 are phenotypically wherein the fact that, in the absence of a restorer gene in their genome, they are male sterile. A male sterile plant is defined as not being able to produce fertile, viable pollen.

Plants harboring MS-BN1 can, for example, be obtained from seeds comprising MS-BN1 deposited at the ATCC under accession number PTA-730. Such plants can be further propagated to introduce the elite event of the invention into other cultivars of the same plant species.

WOSR Plants or plant material comprising RF-BN1 can be identified according to the restriction map identification protocol described for RF-BN1 in Example 5 herein. Briefly, WOSR genomic DNA is digested with a selection (preferably two to four) of the following restriction enzymes: BamHI, EcoRI, EcoRV, and HindIII, is then transferred to nylon membranes and hybridized with the 2182 bp HpaI fragment of plasmid pTHW118 (or of the T-DNA comprised therein). It is then determined for each restriction enzyme used whether the following fragments can be identified:

BamHI: one fragment of between 805 and 1099 bp, preferably of about 814 bp, one fragment of between 1700 and 1986 bp, preferably of about 1849 bp, one fragment of between 2450 and 2838 bp, preferably of about 2607 bp, and one fragment of between 5077 and 14057 bp, preferably of about 6500 bp;

EcoRI: one fragment of between 805 and 1159 bp, preferably of about 1094 bp, one fragment of between 1986 and 2450 bp, preferably of about 2149 bp, and two fragments of between 5077 and 14057 bp, preferably one of about 7000 bp, and one of about 10 kbp;

EcoRV: two fragments of between 5077 and 14057 bp, preferably one of about 5.4 kbp and of about 8 kbp and;

HindIII: one fragment of between 1700 and 1986 bp, preferably of about 1969 bp, and two fragments of between 2450 and 2838 bp, preferably one of about 2565 bp, and one of about 2635 bp.

The lengths of the DNA fragments are determined by comparison with a set of DNA fragments of known length, particularly the PstI fragments of phage lambda DNA.

If the plant material after digestion with at least two, preferably at least 3, more particularly with all of these restriction enzymes, yields DNA fragments with the same length as those described above, the WOSR plant is determined to harbor elite event RF-BN1.

Plants or plant material comprising RF-BN1 can also be identified according to the PCR identification protocol described for RF-BN1 in Example 5 herein. Briefly, WOSR genomic DNA is amplified by PCR using a primer which specifically recognizes a flanking sequence of RF-BN1, preferably the 5' or 3' flanking sequence of RF-BN1 described herein, particularly the primer with the sequence of SEQ ID NO:41, and a primer which recognizes a sequence in the transgene, particularly the primer with the sequence of SEQ ID NO:23. Endogenous WOSR primers are used as controls. If the plant material yields a fragment of between 195 and 235 bp, preferably of about 215 bp, the WOSR plant is determined to harbor elite event RF-BN1.

Plants harboring RF-BN1 are wherein the fact that barstar is expressed in the cells of the tapetum. The production of barstar in the tapetum cells of the plant has been shown to be neither beneficial nor detrimental to the production of pollen (Mariani et al. 1992, above). Thus, in the absence of a male sterility gene in the genome of the plant, the TA29-barstar gene will not result in an observable phenotype. In the presence of a male-sterility gene in the genome of the plant, the TA29-barstar gene will result in a fertility restored i.e., fertile phenotype. A plant with a fertility restored phenotype is defined as a plant which, despite the presence of a male sterility gene in its genome, is capable of producing fertile, viable pollen.

Plants harboring RF-BN1 can, for example, be obtained from seeds deposited at the ATCC under accession number PTA-730. Such plants can be further propagated and/or used in a conventional breeding scheme to introduce the elite event of the invention into other cultivars of the same plant species.

Plants harboring MS-BN1 and/or RF-BN1 are also wherein their glufosinate tolerance, which in the context of the present invention includes that plants are tolerant to the herbicide Liberty™. Tolerance to Liberty™ is defined by the criterion that spraying of the plants in the three to four leaf stage (3V to 4V) with at least 200 grams active ingredient/hectare (g.a.i./ha), preferably 400 g.a.i./ha, and possibly up to 1600 g.a.i./ha, does not kill the plants. Plants harboring MS-BN1 and/or RF-BN1 can further be wherein the presence in their cells of phosphinothricin acetyl transferase as determined by a PAT assay (De Block et al, 1987, supra).

The WOSR plants of this invention can be cultivated in a conventional way. The presence of the 35S-bar gene ensures that they are tolerant to glufosinate. Therefore, weeds in the fields where such WOSR plants are grown can be controlled by application of herbicides comprising glufosinate as an active ingredient (such as Liberty™).

Plants harboring MS-BN1 and/or RF-BN1 are also wherein having agronomical characteristics that are comparable to commercially available WOSR varieties in the US. The agronomical characteristics of relevance are: plant height, strength/stiffness of straw, tendency to lodge, winter-hardiness, shatter resistance, drought tolerance, disease resistance (Black leg, Light leafspot, Sclerotinia) and grain production and yield.

It has been observed that the presence of the foreign DNA in the insertion regions of the *B. napus* WOSR plant genome described herein, more particularly at these insertion sites in the *B. napus* WOSR plant genome, confers particularly interesting phenotypic and molecular characteristics to the plants comprising these events. More specifically, the presence of the foreign DNA in these particular regions in the genome of these plants results in stable phenotypic expression of the transgenes without significantly compromising any aspect of desired agronomic performance of the plants, making them particularly suited for the production of hybrid WOSR. Thus, the insertion regions, corresponding to SEQ ID NO:22 and SEQ ID NO:34, more particularly the insertion site of MS-BN1 and RF-BN1 therein, is shown to be particularly suited for the introduction of a gene(s) of interest. More particularly, the insertion regions of MS-BN1 (SEQ ID NO:22) and of RF-BN1 (SEQ ID NO:34), or the insertion sites of MS-BN1 and RF-BN1 respectively therein, are particularly suited for the introduction of plasmids comprising a male-sterility gene and a fertility restorer gene respectively ensuring optimal expression of each of these genes or of both genes in a plant without compromising agronomic performance.

A recombinant DNA molecule can be specifically inserted in an insertion region by targeted insertion methods. Such methods are well known to those skilled in the art and comprise, for example, homologous recombination using a recombinase such as, but not limited to either FLP recombinase from *Saccharomyces cerevisiae* (U.S. Pat. No. 5,527, 695), the CRE recombinase from *Escherichia coli* phage P1 (published PCT application WO 9109957, the recombinase from pSRI of *Saccharomyces rouxii* (Araki et al. (1985) J. Mol. Biol. 182:191–203), or the lambda phage recombination system such as described in U.S. Pat. No. 4,673,640.

As used herein, "sequence identity" with regard to nucleotide sequences (DNA or RNA), refers to the number of positions with identical nucleotides divided by the number of nucleotides in the shorter of the two sequences. The alignment of the two nucleotide sequences is performed by the Wilbur and Lipmann algorithm (Wilbur and Lipmann, 1983) using a window-size of 20 nucleotides, a word length of 4 nucleotides, and a gap penalty of 4. Computer-assisted analysis and interpretation of sequence data, including sequence alignment as described above, can, e.g., be conveniently performed using the programs of the Intelligenetics™ Suite (Intelligenetics Inc., CA). Sequences are indicated as "essentially similar" when such sequence have a sequence identity of at least about 75%, particularly at least about 80%, more particularly at least about 85%, quite particularly about 90%, especially about 95%, more especially about 100%, quite especially are identical. It is clear than when RNA sequences are said to be essentially similar or have a certain degree of sequence identity with DNA sequences, thymine (T) in the DNA sequence is considered equal to uracil (U) in the RNA sequence.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA sequence that is functionally or structurally defined, may comprise additional DNA sequences, etc.

The following examples describe the development and characteristics of WOSR plants harboring the elite events MS-BN1 and RF-BN1.

Unless otherwise stated, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy published by BIOS Scientific Publications Ltd (UK) and Blackwell Scientific Publications, UK.

In the description and examples, reference is made to the following sequences:
SEQ ID NO:1: plasmid pTHW107
SEQ ID NO:2: plasmid pTHW118
SEQ ID NO:3: primer 248
SEQ ID NO:4: primer 249
SEQ ID NO:5: primer 247
SEQ ID NO:6: primer 250
SEQ ID NO:7: primer 251
SEQ ID NO:8: primer 254
SEQ ID NO:9 primer 258
SEQ ID NO:10: primer SP6
SEQ ID NO:11: primer T7
SEQ ID NO:12: primer 201 (BNA01)
SEQ ID NO:13: sequence comprising the 5' flanking region of MS-BN1
SEQ ID NO:14: primer 611
SEQ ID NO:15: primer 259
SEQ ID NO:16: primer 260
SEQ ID NO:17: primer 24
SEQ ID NO:18: sequence comprising the 3' flanking region of MS-BN1
SEQ ID NO:19: primer 51 (BNA02)
SEQ ID NO:20: primer 48
SEQ ID NO:21: sequence comprising the target site deletion of MS-BN1
SEQ ID NO:22: insertion-region MS-BN1
SEQ ID NO:23: primer 193 (BNA03)
SEQ ID NO:24: sequence comprising the 5' flanking region of RF-BN1
SEQ ID NO:25: primer 286
SEQ ID NO:26: primer 314
SEQ ID NO:27: primer 315
SEQ ID NO:28: primer 316
SEQ ID NO:29: primer 288
SEQ ID NO:30: sequence comprising the 3' flanking region of RF-BN1
SEQ ID NO:31: primer 269
SEQ ID NO:32: primer 283
SEQ ID NO:33: primer 284
SEQ ID NO:34: integration region RF-BN1
SEQ ID NO:35: primer 57
SEQ ID NO:36: sequence comprising the 5' flanking region of MS-BN1 in WOSR
SEQ ID NO:37: primer 68
SEQ ID NO:38: sequence comprising the 3' flanking region of MS-BN1 in WOSR
SEQ ID NO:39: sequence comprising the 5' flanking region of RF-BN6 in WOSR
SEQ ID NO:40: sequence comprising the 3' flanking region of RF-BN1 in WOSR
SEQ ID NO:41: primer 268 (BNA04)
SEQ ID NO:42: primer BNA05
SEQ ID NO:43: primer BNA06

EXAMPLE 1

Transformation of *B. napus* with a Male-Sterility Gene and a Restorer Gene a) Construction of the Chimeric DNA Comprising the Barnase Gene Under the Control of a Tapetum Specific Promoter (pTHW107).

Plasmid pTHW107 (SEQ ID NO:1) was essentially derived from the intermediate vector pGSV1. PGSV1 is itself derived from pGSC1700 (Cornelissen and Vandewielle, 1989), but comprises an artificial T-region consisting of the left and right border sequences of the TL-DNA form pTiB6S3 and multilinker cloning sites allowing the insertion of chimeric genes between the T-DNA border repeats. The pGSV1 vector is provided with a barstar gene on the plasmid mainframe, with regulatory signals for expression in *E. coli*.

A full description of the DNA comprised between the border repeats of pTHW107 is given in Table 1.

TABLE 1

T-DNA of plasmid pTHW107

| nt positions | Orientation | Description and references |
|---|---|---|
| 1–25 | | Right border repeat from the TL-DNA from pTiB6S3 (Gielen et al (1984) EMBO J. 3:835–846). |
| 26–97 | | Synthetic polylinker derived sequences |
| 309–98 | Counter clockwise | The 3' untranslated end from the TL-DNA gene 7 (3' g7) of pTiB6S3 (Velten and Schell (1985) Nucl. Acids Res. 13:6981-6998; Dhaese et al. (1983) EMBO J. 3:835-846). |
| 310–330 | | Synthetic polylinker derived sequences |
| 882–331 | Counter clockwise | The coding sequence of the *bar* gene of *Streptomyces hygroscopicus* (Thompson et al. (1987) EMBO J. 6:2519–2523). The N-terminal two codons of the wild type *bar* coding region have been substituted for the codons ATG and GAC respectively. |
| 2608–883 | Counter clockwise | The promoter from the atSlA ribulose-1,5-biphosphate carboxylase small subunit gene from *Arabidopsis thaliana* (PssuAra) (Krebbers et al. (1988) Plant Mol. Biol. 11:745–759). |
| 2609–2658 | | Synthetic polylinker derived sequences |
| 2919–2659 | Counter clockwise | A 260 bp TaqI fragment from the 3' untranslated end of the nopaline synthase gene (3' nos) from the T-DNA of pTiT37 and containing plant polyadenylation signals (Depicker et al. (1982) J. Mol. Appl. Genet. 1:561–573). |
| 2920–3031 | | 3' untranslated region downstream from the *barnase* coding sequence of *B. amyloliquefaciens* |
| 3367–3032 | Counter clockwise | The coding region of the *barnase* gene from *Bacillus amyloliquefaciens* (Hartley (1988) J. Mol. Biol. 202:913–915). |
| 4877–3368 | Counter clockwise | The promoter region of the anther-specific gene TA29 from *Nicotiana tabacum*. The promoter comprises the 1.5 kb of the sequence upstream from the ATG initiation codon (Seurinck et al. (1990) Nucl. Acids Res. 18:3403). |
| 4878–4921 | | Synthetic polylinker derived sequences |
| 4922–4946 | | Left border repeat from the TL-DNA from pTiB6S3 (Gielen et al (1984) EMBO J. 3:835–846). | b) Construction of the Chimeric DNA Comprising the Barstar Gene Under the Control of a Constitutive Promoter (pTHW118)

Plasmid pTHW118 (SEQ ID NO:2) was also essentially derived from the intermediate vector pGSV1 (described above). A full description of the DNA comprised between the border repeats of pTHW118 is given in Table 2:

TABLE 2

T-DNA of plasmid pTHW118

| nt positions | Orientation | Description and references |
|---|---|---|
| 1–25 | | Right border repeat from the TL-DNA from pTiB6S3 (Gielen et al (1984) |
| 26–53 | | Synthetic polylinker derived sequences |
| 54–90 | | Residual sequence from the TL-DNA at the right border repeat. |
| 91–97 | | Synthetic polylinker derived sequences. |
| 309–98 | Counter clockwise | 3' untranslated end from the TL-DNA gene 7 (3' g7) of pTiB6S3 (Velten and Schell (1985); Dhaese et al. (1983) |
| 310–330 | | Synthetic polylinker derived sequences |
| 883–331 | Counter clockwise | The coding sequence of the bialaphos resistance gene (*bar*) of *Streptomyces hygroscopicus* (Thompson et al. (1987). The N-terminal two codons of the wild type *bar* coding region have been substituted for the codons ATG and GAC respectively. |
| 2608–883 | Counter clockwise | The promoter from the atSlA ribulose-1,5-biphosphate carboxylase small subunit gene from *Arabidopsis thaliana* (PssuAra) (Krebbers et al. (1988) |
| 2609–2658 | | Synthetic polylinker derived sequences |
| 2919–2659 | Counter clockwise | A 260 bp TaqI fragment from the 3' untranslated end of the nopaline synthase gene (3' nos) from the T-DNA of pTiT37 and containing plant polyadenylation signals (Depicker et al. (1982) |
| 2920–2940 | | Synthetic polylinker derived sequences |
| 2941–2980 | | 3' untranslated region downstream from the *barstar* coding sequence from *Bacillus amyloliquefaciens* |
| 3253–2981 | Counter clockwise | The coding region of the *barstar* gene from *Bacillus amyloliquefaciens* (Hartley (1988) |
| 4762–3254 | Counter clockwise | The promoter region of the anther-specific gene TA29 from *Nicotiana tabacum*. The promoter comprises the 1.5 kb of the sequence upstream from the ATG initiation codon (Seurinck et al. (1990) |
| 4763–4807 | | Synthetic polylinker derived sequences |
| 4808–4832 | | Left border repeat from the TL-DNA from pTiB6S3 (Gielen et al (1984) | c) Transformation of *B. napus*

For transformation of *B. napus* the vector system as described by Deblaere et al. (1985, 1987) was used. The vector system consists of an Agrobacterium strain and two plasmid components: 1) a non-oncogenic T1-plasmid (pGV400) and 2) an intermediate cloning vector based on plasmid pGSV1. The non-oncogenic Ti-plasmid from which the T-region has been deleted carries the vir genes required for transfer of an artificial T-DNA cloned on the second plasmid to the plant genome. The Agrobacterium strains resulting from the triparental mating between these components can be used for plant transformation.

Selection was done on phosphinothricin (PPT) at all stages except plantlet regeneration, which was done in the absence of PPT to accelerate growth. This resulted in a set of primary transformants (plants of generation NO:).

EXAMPLE 2

Development of Events 2.1. Characterization of Transgenic Events 2.1.1. Southern Blot Analysis of MS Events Presence of the transgene and the number of gene insertions were checked by standard Southern blot analysis. Total genomic DNA is isolated from 1 g of shoot tissue according to Dellaporta ((1983) Plant Mol. Biol. Rep. 3:19–21; or Doyle et al. (1987) Phytochem. Bull. 19:11) and digested with Sacd restriction enzyme. Sacd has a unique restriction site within the T-DNA fragment, situated between the barnase and bar constructs. Southern analysis was performed with the following two probes:

"barnase" probe: 478 bp PstI-EcoRI fragment of plasmid pVE113

"bar" probe: 546 bp NcoI-BglII fragment of plasmid pDE110

Plasmid pVE113 and pDE110 are described in FIG. 1 and WO 92/09696 respectively.

Hybridization of the MS events with the barnase probe yielded a 12 Kb band, while hybridization with the bar probe yielded a 14 Kb fragment.

The relative band intensity provided an indication on whether plants were homozygous or hemizygous for the transgenic locus. Two events were found to have simple insertions. This was confirmed by the fact that the segregation pattern of the transgene could be explained by Mendelian inheritance of a simple locus.

2.1.2. Southern Blot Analysis of RF Events

Presence of the transgene and the number of gene insertions were checked by standard Southern blot analysis. Total genomic DNA was isolated from 1 g of shoot tissue (according to Doyle et al. (1987) Phytochem. Bull. 19:11) and digested with SacI restriction enzyme. SacI has a unique restriction site within the T-DNA fragment, situated between the barnase and bar constructs. Southern analysis was performed with the following two probes:

"barstar" probe: 436 bp HindIII-PstI fragment of plasmid pVE113

"bar" probe: 546 bp NcoI-BglII fragment of plasmid pDE110

Hybridization of the RF events with the barstar probe yielded a 3 Kb band, while hybridization with the bar probe yielded a 14 Kb fragment.

The relative band intensity provided an indication on whether plants were homozygous or hemizygous for the transgenic locus. Several events were found to have simple insertions. This was confirmed by the fact that the segregation pattern of the transgene could be explained by Mendelian inheritance of a simple locus.

2.1.3. General Plant Phenotype and Agronomic Performance

T1 plants of both MS and RF events were evaluated for a number of phenotypic traits including plant height, strength/stiffness of straw, tendency to lodge, shatter resistance, drought tolerance, disease resistance (Black leg, Light leafspot, Sclerotinia) and grain production and yield.

Lines were evaluated to be similar (or improved) in displayed agronomic characteristics compared to the untransformed variety as well as a number of oilseed rape cultivars. In some cases, the plants segregated for somatoclonal variation for one or more of the above-mentioned traits. Unless this resulted in the introduction of a commercially interesting phenotypic trait, these plants were discarded.

2.2. Development of Lines Carrying the MS or RF Trait

The various T0: hemizygous plantlets ("Ms/–" or "Rf/–") were transitioned from tissue culture, transferred to greenhouse soil. Presence of the transgene and copy number was checked by southern blot analysis (described above). The plants were allowed to flower and sterility or fertility of flowers was evaluated respectively. The T0 plants were crossed with wildtype plants (–/–) to produce T1 seed (MsT1 and RfT1). T1 seeds were planted and grown up in the greenhouse. Plants were evaluated for tolerance to glufosinate ammonium. Ms-T1 plants were also evaluated for sterility/fertility segregation (in non-sprayed plants), while Rf-T1 plants were checked for fertile flowers.

Ms-T1 plants comprising the transgene were crossed with a tester plant homozygous for a fertility restorer gene (Rf/Rf), for the production of MsRf-F1 seed. This seed (Ms/–, Rf/– and –/–, Rf/–) was planted in the greenhouse and sprayed with Liberty™. Remaining F1 progeny is evaluated for fertility/sterility segregation to test whether the male sterility trait could be adequately restored in B. napus (fertility close to 100%).

The best events were selected for further testing. Ms-T1 plants were crossed with a homozygous fertility restorer and the seed was planted in the field. Plants were evaluated for tolerance to the Liberty™ herbicide (at 800 grams active ingredient per hectare (g.a.i./ha) recommended dosage for farmers is 400 g.a.i./ha), for fertility/sterility segregation and for general phenotypic characteristics. The lines in which fertility was 100% restored and for which no negative penalties on phenotype or agronomic performance (detailed under (d)) was observed as compared to the wild-type isogenic control were selected.

Rf-T1 plants comprising the transgene were crossed with a tester plant comprising the male sterility gene (Ms/–), for the production of F1 seed. This seed was planted in the greenhouse, sprayed with Liberty™ and restoration of fertility was evaluated (close to 100%).

Meanwhile Rf-T1 plants are selfed to produce S1. The S1 plants are grown in the greenhouse, sprayed with Liberty™ and again selfed to produce S2; from the S2, homozygous individuals were selected.

2.3. Combination of MS and RF Events.

The selected Ms-T1 plants were crossed with the selected Rf-S2 events in the greenhouse for fertility restoration testing. The seed was replanted in the greenhouse, plants were sprayed with Liberty™ and fertility of the flowers was checked.

2.4. Testing MS and RF Events in Different Genetic Backgrounds and Locations

The selected events were introduced into two different genetic backgrounds that are heterotically distinct, to prove that the MS and RF events function well and have no negative penalty on yield or quality in any background tested.

At the same time the selected MS and RF events are tested in four to five different environments to ensure that there is no negative interaction between environment and the MS or RF events.

In a next stage the production of hybrid seed using the selected MS and RF events was tested more extensively in the field. The selected MS event in its original background and in two different and heterotically distinct backgrounds was crossed with the selected RF event in its original background and two different and heterotically distinct backgrounds. The F1 hybrid was evaluated for resistance to Liberty™, for fertility, as well as overall agronomic performance (yield and quality).

2.5. Selection of Elite Events

The above described selection procedure in the development of transgenic MS lines, yielded several elite events which displayed optimal expression of the transgene, i.e. resistance to glufosinate ammonium, a male-sterile phenotype and susceptibility to complete fertility restoration with a homozygous restorer line, more specifically with the selected RF elite event.

The above described selection procedure in the development of transgenic RF lines, yielded several elite events which displayed optimal expression of the transgene, i.e. resistance to the glufosinate ammonium and the ability to restore fertility of the F1 when crossed with a plant carrying a male sterility gene, more specifically with the selected MS elite event.

EXAMPLE 3

Introduction of Candidate Elite Events Selected into WOSR

Several MS and RF elite events developed in *B. napus* as described above were introduced by repeated backcrossing of Drakkar variety plants, into a WOSR cultivar.

Plants were examined and it was established that:
a) the presence of the foreign DNA did not compromise other desired characteristics of the plant, such as those relating to agronomic performance or commercial value;
b) the event was wherein a well defined molecular configuration which was stably inherited;
c) the gene(s) of interest in the foreign DNA showed a correct, appropriate and stable spatial and temporal phenotypic expression, both in heterozygous (or hemizygous) and homozygous condition of the event, at a commercially acceptable level in a range of environmental conditions in which the plants carrying the event are likely to be exposed in normal agronomic use.

Furthermore, the plants were evaluated for their agronomical characteristics and performance as compared with wild-type WOSR species.

Extensive testing in the field demonstrated that certain candidate elite events of spring oilseed rape, when introduced into WOSR resulted in plants which showed adequate expression of the genes of interest in the foreign DNA, combined with optimal agronomic performance. These events were selected as MS and RF elite events in WOSR and were named MS-BN1 and RF-BN1 respectively.

EXAMPLE 4

Characterization of Elite Events MS-BN1 and RF-BN1

Once the MS-BN1 and RF-BN1 events were identified as the elite events in which expression of the respective transgenes as well as overall agronomic performance were optimal, the loci of the transgenes were analyzed in detail on a molecular level. This included detailed Southern blot analysis (using multiple restriction enzymes) and sequencing of the flanking regions of the transgene.

4.1. Southern Blot Analysis Using Multiple Restriction Enzymes

Leaf tissue was harvested from transgenic and control plants. Total genomic DNA was isolated from leaf tissue according to Dellaporta et al. (1983). The DNA concentration of each preparation was determined by measuring the optical density in a spectrophotometer at a wavelength of 260 nm.

10 µg of genomic DNA was digested with restriction enzyme in a final reaction volume of 40 µl, applying conditions proposed by the manufacturer. The time of digestion and/or amount of restriction enzyme were adjusted to ensure complete digestion of the genomic DNA samples without non-specific degradation. After digestion, 4 µl of loading dye was added to the digested DNA samples, and they were loaded on a 1% agarose gel.

The following control DNAs were also loaded on the gel:
a negative control with genomic DNA prepared from a non-transgenic Brassica plant. This negative control is used to confirm the absence of background hybridization.
a DNA positive control: With a heterozygous single copy integration of the transgene into the *B. napus* genome, 10 jig of genomic DNA has the same number of molecule equivalents as ±19 picogram of 1501 bp PvuI-HindIII fragment of pTHW118 DNA (*B. napus* diploid genome size: $0.8 \times 10^9$ bp). The amount representing one plasmid copy per genome is added to 1 µg of digested non-transgenic *B. napus* DNA. This reconstitution sample is used to show that the hybridizations are performed under conditions allowing hybridization of the probe with target sequences.

Phage Lambda DNA (strain CIind 1 ts 857 Sam 7, Life Technologies) digested with PstI was included as size standard.

After electrophoresis, the DNA samples (digested Brassica genomic DNA, controls and size standard DNA) were transferred to a Nylon membrane by capillary blotting during 12 to 16 hours.

The DNA templates used for probe preparation for MS-BN1 events were prepared by restriction digestion of PTW107 with HindIII. This released a 3942 bp DNA fragment that encompasses a relevant part of the transforming DNA (part of PSSUARA, 3'nos, barnase, PTA29).

The DNA templates used for probe preparation for RF-BN1 events were prepared by restriction digestion of PTW118 with Hpal. This released a 2182 bp DNA fragment that encompasses a relevant part of the transforming DNA (part of PSSUARA, 3'nos, barstar, PTA29).

After purification, the DNA fragments were labeled according to standard procedures, and used for hybridizing to the membrane.

Hybridization was performed under standard stringency conditions: The labeled probe was denatured by heating for 5 to 10 minutes in a water bath at 95° C. to 100° C. and chilling on ice for 5 to 10 minutes and added to the hybridization solution (6×SSC (20×SSC is 3.0 M NaCl, 0.3 M Na citrate, pH 7.0), 5×Denhardt's (100×Denhardt's =2% Ficoll, 2% Polyvinyl pyrollidone, 2% Bovine Serum Albumin), 0.5% SDS and 20 µg/ml denatured carrier DNA (single-stranded fish sperm DNA, with an average length of 120–3000 nucleotides). The hybridization was performed overnight at 65° C. The blots were washed three times for 20 to 40 minutes at 65° C., with the wash solution (2×SSC, 0.1% SDS). The autoradiographs were electronically scanned.

4.1.1. MS-BN1

Figure 2:
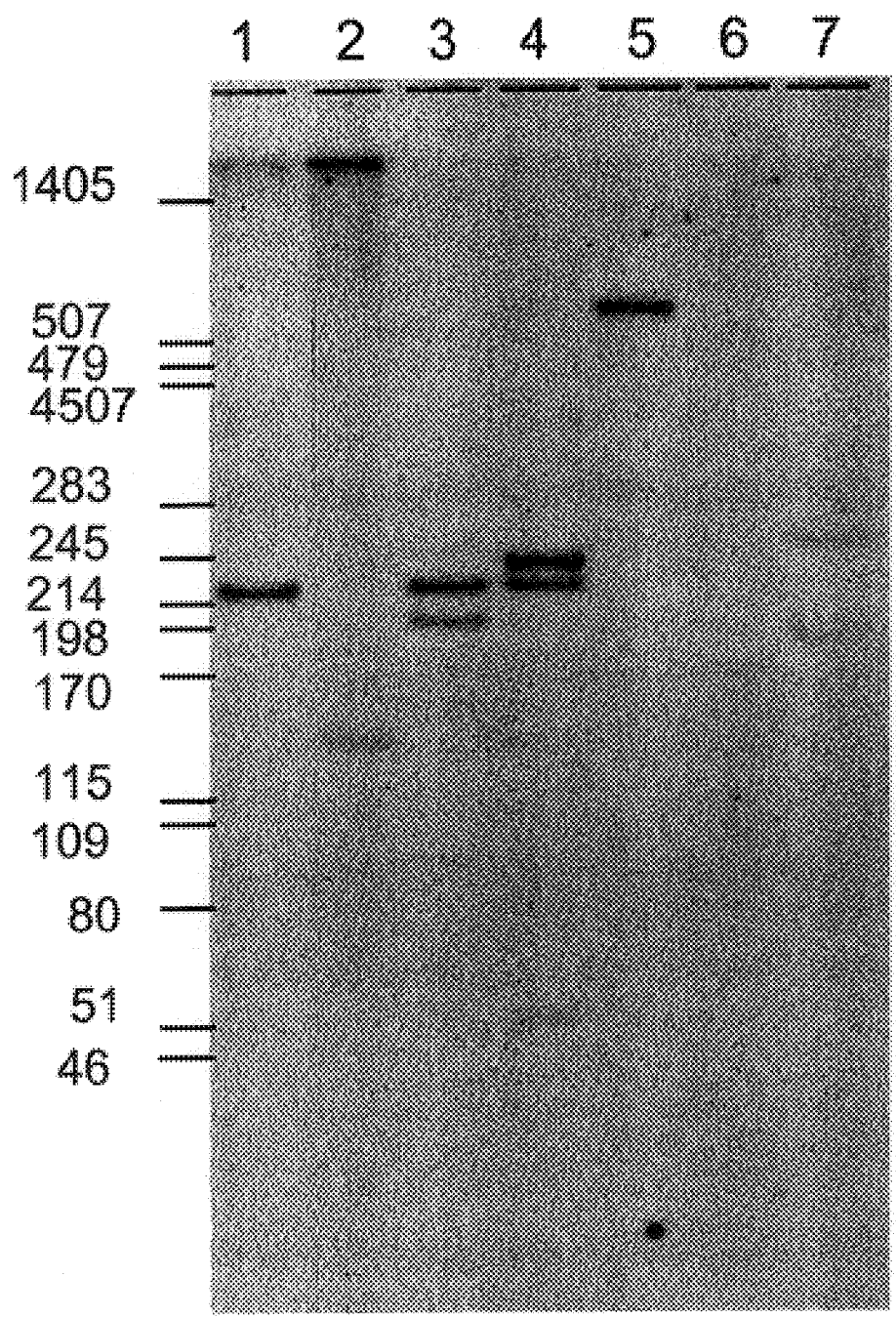
FIG. 2 depicts a restriction map obtained after digestion of MS-BN1 genomic DNA. Loading sequence of the gel analyzed by Southern blot: lane 1, MS-BN1 DNA digested with EcoRI, lane 2, MS-BN1 DNA digested with EcoRV, lane 3, MS-BN1 DNA digested with HpaI, lane 4, MS-BN1 DNA digested with AflIII, lane 5, MS-BN1 DNA digested with NdeI, lane 6, non-transgenic WOSR DNA digested with BamHI, lane 7, non-transgenic WOSR digested with BamHI+control plasmid pTHW107 DNA digested with BamHI.

The restriction patterns obtained after digestion of MS-BN1 genomic DNA with different restriction enzymes is presented in FIG. 2 and summarized in Table 3.

TABLE 3

Restriction map of MS-BN1

| Lane number | DNA loaded | Migration of hybridizing DNA fragments between size marker bands | | Estimated length of the hybridizing DNA fragments |
|---|---|---|---|---|
| | | Larger than | Smaller than | |
| 1 | MS-BN1-EcoRI | 2140 | 2450 | 2266 bp (*) |
| | | 14057 | — | >14 kbp |
| 2 | MS-BN1-EcoRV | 1159 | 1700 | 1.4 kbp (*) |
| | | 14057 | — | >14 kbp |
| 4 | MS-BN1-HpaI | 1986 | 2140 | 1990 bp |
| | | 2140 | 2450 | 2229 bp |
| 5 | MS-BN1-AflIII | 2450 | 2838 | 2477 bp (*) |
| | | 2140 | 2450 | 2250 bp |
| | | 514 | 805 | 552 bp (*) |
| 6 | MS-BN1-NdeI | 5077 | 14057 | 10 kbp |
| | | 5077 | 14057 | 6510 bp |

TABLE 3-continued

Restriction map of MS-BN1

| Lane number | DNA loaded | Migration of hybridizing DNA fragments between size marker bands | | Estimated length of the hybridizing DNA fragments |
|---|---|---|---|---|
| | | Larger than | Smaller than | |
| 7 | Non-transgenic WOSR | — | — | — |
| 8 | Control plasmid DNA-BamHI | 1700<br>2450 | 1986<br>2838 | 1966 bp (*)<br>2607 bp (*) |

(*) the lengths of these fragments are those predicted from the restriction map of the plasmid pTHW107

4.1.2. RF-BN1

Figure 3:
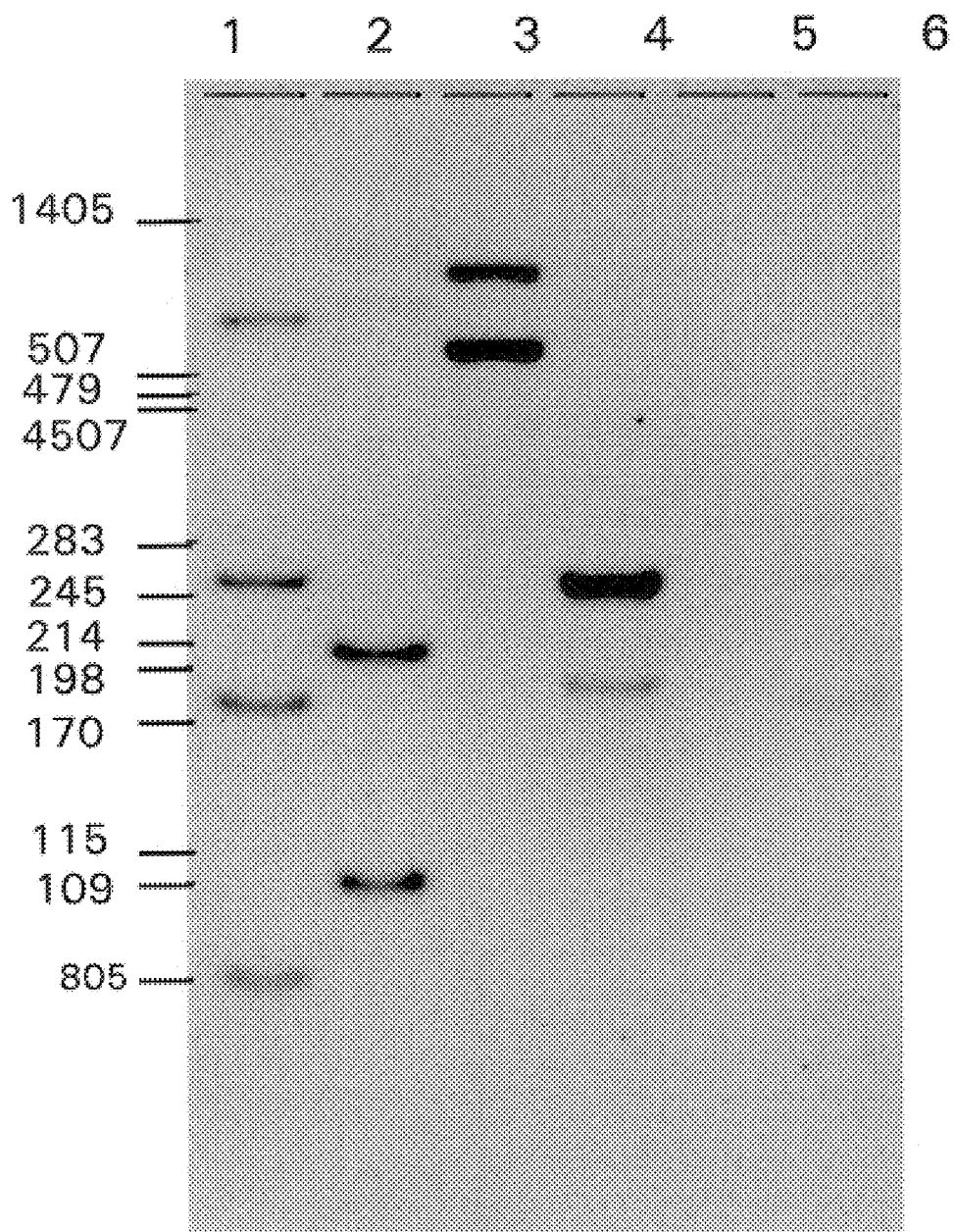
FIG. 3 depicts a restriction map obtained after digestion of RF-BN1 genomic DNA. Loading sequence of the gel analyzed by Southern blot: lane 1, RF-MS 1 DNA digested with BamHI, lane 2, RF-BN1 DNA digested with EcoRI, lane 3, RF-BN1 DNA digested with EcoRV, lane 4, RF-BN1 DNA digested with HindIII, lane 5, non-transgenic WOSR DNA digested with BamHI, lane 6, non-transgenic WOSR digested with BamHI+control plasmid pTHW118 DNA digested with BamHI.

The restriction patterns obtained after digestion of RF-BN1 genomic DNA with different restriction enzymes is presented in FIG. 3 and summarized in Table 4.

TABLE 4

Restriction map of RF-BN1

| Lane number | DNA loaded | Migration of hybridizing DNA fragments between size marker bands | | Estimated length of the hybridizing DNA fragments |
|---|---|---|---|---|
| | | Larger than | Smaller than | |
| 1 | MS-BN1-BamHI | 805<br>1700<br>2450<br>5077 | 1099<br>1986<br>2838<br>14057 | 814 bp<br>1849 bp (*)<br>2607 bp (*)<br>6580 bp |
| 2 | MS-BN1-EcoRI | 805<br>1986<br>5077<br>5077 | 1159<br>2450<br>14057<br>14057 | 1094 bp<br>2149 bp<br>7000 bp<br>10 kbp |
| 3 | MS-BN1-EcoRV | 5077<br>5077 | 14057<br>14057 | 5.4 kbp<br>8 kbp |
| 4 | MS-BN1-HindIII | 1700<br>2450<br>2450 | 2140<br>2838<br>2838 | 1969 bp<br>2565 bp<br>2635 bp |
| 6 | Non-transgenic WOSR | — | — | — |
| 5 | Control plasmid DNA-BamHI | 1700<br>2450<br>5077 | 1986<br>2838<br>14057 | 1849 bp (*)<br>2607 bp (*)<br>8100 bp |

(*) the lengths of these fragments are those predicted from the restriction map of the pTHW118 vector with BamHI.

4.2. Identification of the Flanking Regions

Flanking regions of the elite events MS-BN1 and RF-BN1 were first identified for spring OSR, in which the events were developed, and then checked for WOSR.

4.2.1. Identification of the Flanking Regions of MS-BN1

4.2.1.1. Right (5') Flanking Region

The sequence of the right border flanking region of MS-BN1, a ligation-mediated polymerase chain reaction (Mueller et al. 1989, Science 780–786; Maxine t al., 1994, PCR Methods and Applications, 71–75) with extension capture (Törmanen et al. 1993, NAR 20:5487–5488) was used.

The oligonucleotides used for linker preparation were:

MDB248: (SEQ ID NO:3)
5'CATGCCCTGACCCAGGCTAAGTATTT-TAACTTTAACCACTTTGCTCCGACAG TCCCATTG

MDB249: (SEQ ID NO:4)
5'CAATGGGACTGTCGGAGGACTGAGGGC-CAAAGCTTGGCTCTTAGCCTGGGT CAGGGCATG

Preparation of the linker was followed by first strand synthesis from genomic MS-BN1 DNA digested with NcoI, using a biotinylated gene-specific primer:

| | Sequence (5'→3') | Position in pTHW107 |
|---|---|---|
| Biotinylated primer MDB247 | CCGTCACCGAGATCTGATCTCACGCG<br>(SEQ ID NO:5) | 322←347 |

The linker was then ligated to the first strand DNA, which was then coupled to magnetic beads from which the non-biotinylated strand was eluted. This DNA was used in an upscaled PCR amplification using the following primers:

| | Sequence (5'→3') | Position in pTHW107 |
|---|---|---|
| Linker primer MDB250 | GCACTGAGGGCCAAAGCTTGGCTC<br>(SEQ ID NO:6) | — |
| T-DNA primer MDB251 | GGATCCCCCGATGAGCTAAGCTAGC<br>(SEQ ID NO:7) | 293←317 |

This PCR yielded a fragment of about 1150 bp. This Right Border fragment was eluted out of an agarose gel and a nested PCR was done on a 100 fold dilution of this DNA using the following primers:

| | Sequence (5'→3') | Position in pTHW107 |
|---|---|---|
| Nested linker primer MDB254 | CTTAGCCTGGGTCAGGGCATG<br>(SEQ ID NO:8) | — |
| T-DNA primer MDB258 | CTACGGCAATGTACCAGCTG<br>(SEQ ID NO:9) | 224←243 |

This yielded a fragment of about 1000 bp, which was eluted out of the agarose gel, purified, and ligated to the pGem®-T Vector. The recombinant plasmid DNA was screened using a standard PCR reaction with the following primers:

| | Sequence (5'→3') | Position in pTHW107 |
|---|---|---|
| SP6 primer | TAATACGACTCACTATAGGGCGA<br>(SEQ ID NO:10) | -(SP6 promoter in pGem ®-T Vector) |
| T7 primer | TTTAGGTGACACTATAGAATAC<br>(SEQ ID NO:11) | -(T7 promoter in pGem ®-T Vector) |
| T-DNA primer MDB201 | gCTTGGACTATAATACCTGAC<br>(SEQ ID NO:12) | 143←163 |

This yielded the following fragments:
SP6-T7: 1224 bp
SP6-MDB201: 1068 bp
T7-MDB201: 1044 bp The right border fragment was purified and sequenced (SEQ ID NO:13) resulting in 953 bp of which bp 1–867 corresponds to plant DNA and bp 868 to 953 corresponds to T-DNA of pTHW107.

4.2.1.2. Left (3') Flanking Region of MS-BN1

The sequence of the left border region flanking the inserted transgene in the MS-BN1 event were determined using the thermal asymmetric interlaced (TAIL-) PCR method as described by Liu et al. ((1995) Plant J. 8:457–463). This method utilizes three nested specific primers in successive reactions together with a shorter arbitrary degenerate (AD) primer so that the relative amplification efficiencies of specific and non-specific products can be thermally controlled. The specific primers were selected for annealing to the border of the transgene and based on their annealing conditions. A small amount (5 µl) of unpurified secondary and tertiary PCR products were analyzed on a 1% agarose gel. The tertiary PCR product was used for preparative amplification, purified and sequenced on an automated sequencer using the DyeDeoxy Terminator cycle kit.

The following primers were used:

|  | Sequence (5'→3') | Position in |
|---|---|---|
| Degenerate primer MDB611 | NgTCgASWgTNTWCAA (SEQ ID NO:14) | — |
| Primary TAIL MDB259 | gTgCagggAAgCggTTAACTgg (SEQ ID NO:15) | 7164→4186 |
| Second. TAIL MDB260 | CCTTTggAgTAAATggTgTTgg (SEQ ID NO:16) | 4346→4366 |
| Tertiary TAIL HCA24 | gCgAATgTATATTATATgCA (SEQ ID NO:17) | 4738→4757 | whereby: N = A, C, T or g; S = C or g; W = A or T

The fragment amplified using HCA24-MDB611 was ca. 540 bp of which 537 bp were sequenced (3'flank: SEQ ID NO:18). The sequence between bp 1 and bp 180 comprised pTHW107 DNA, while the sequence between bp 181 and bp 537 corresponded to plant DNA.

4.2.1.3. Identification of the Target Site Deletion

Using primers corresponding to sequences within the flanking regions of the transgene on the wildtype *B. napus* var. Drakkar as a template, the insertion site of the transgene was identified.

The following primers were used:

|  | Sequence (5'→3') | Position in 5' flank (SEQ ID NO:13) | Position in 3' flank (SEQ ID NO:18) |
|---|---|---|---|
| VDS51 | TgACACTTTgAgCCACTCg (SEQ ID NO:19) | 733→751 | — |
| HCA48 | GgAgggTgTTTTTggTTATC (SEQ ID NO:20) | — | 189←208 |

This yielded a 178 bp fragment (SEQ ID NO:21) in which bp 132 to 150 corresponds to a target site deletion.

4.2.1.4. Identification of the MS-BN1 Insertion Region

Based on the identification of the flanking regions, and the target site deletion the insertion region of MS-BN1 could be determined (SEQ ID NO:22):

1–822:5' flanking region bp 46–867 of SEQ ID NO:13
823–841 target site deletion bp 132–150 of SEQ ID NO:21
842–1198: 3' flanking region bp 181 to 537 of SEQ ID NO:18

4.2.2. Identification of the Flanking Regions of RF-BN1

The border flanking regions of RF-BN1 were determined by Vectorette-PCR (Use of Vectorette and Subvectorette PCR to isolate transgene flanking DNA, Maxine J. Allen, Andrew Collick, and Alec J. Jeffreys PCR Methods and Applications—1994 (4) pages 71–75) with RF-BN1 genomic DNA digested with HindIII as a template. The vectorette linker was made using the primers MDB248 (SEQ ID NO:3) and MDB249 (SEQ ID NO:4) primers described above.

4.2.2.1. Right (5') Flanking Region of BN-RF1

The following primers were used:

|  | Sequence (5' → 3') | Position in pTHW118 |
|---|---|---|
| Vectorette primer MDB250 | GCACTGAGGGCCAAAGCTTGGC TC (SEQ ID NO:6) | — |
| Vectorette primer MDB254 | CTTAGCCTGGGTCAGGGCATG (SEQ ID NO:8) | — |
| T-DNA primer MDB251 | GGATCCCCCGATGAGCTAAGCT AGC (SEQ ID NO:7) | 293←317 |
| T-DNA primer MDB193 | TCATCTACGGCAATGTACCAGC (SEQ ID NO:23) | 226←247 |
| T-DNA primer MDB258 | CTACGGCAATGTACCAGCTG (SEQ ID NO:9) | 224←243 |
| T-DNA primer MDB201 | GCTTGGACTATAATACCTGAC (SEQ ID NO:12) | 143←163 |

This yielded a 1077 bp fragment (SEQ ID NO:24) in which bp 46–881 corresponds to plant DNA and bp 882–1060 corresponds to T-DNA of pTHW118.

4.2.2.2. Left (3') Flanking Region of BN-RF1

To identify the 3' flanking region of elite event BN-RF1, a TAIL PCR was performed as described above using an Arbitrary degenerate primer and primers located in the T-DNA in the vicinity of the left border.

The primers used were:

Arbitrary Degenerate Primer:

MDB286 NTgCgASWgANAWgAA (SEQ ID NO:25)

whereby: N=A,C,T or g; S=C or g; W=A or T

| MDB314 | gTAggAggTTgggAAgACC | (SEQ ID NO:26) |
| MDB315 | gggCTTTCTACTAgAAAgCTCTCg.g | (SEQ ID NO:27) |
| MDB316 | CCgATAgggAAgTgATgTAggAgg | (SEQ ID NO:28) |

A fragment of about 2000 bp was obtained. This fragment was cloned in a pGem®-T Vector and used as a template for a PCR reaction using the following primers:

Plant DNA Primer:

| Plant DNA primer: MDB288 | ATgCAgCAAgAAgCTTggAgg | (SEQ ID NO:29) |
| T-DNA primer: MDB314 | gTAggAggTTgggAAgACC | (SEQ ID NO:26) |

This yielded a fragment of about 1500 bp (SEQ ID NO:30) wherein bp 17–182 corresponds to T-DNA from plasmid pTHW118 and bp 183–1457 corresponds to plant DNA.

4.2.2.3. Molecular Analysis of the Target-Site Deletion

The target site deletion was cloned with the TAIL-PCR method (described above), using wild type genomic DNA and plant DNA specific primers upstream of the T-DNA insert directed towards the insert:

Arbitrary Degenerate Primer:
MDB286 NTgCgASWgANAWgAA (SEQ ID NO:25)
whereby: N=A,C,T or g; S=C or g; W=A or T

| MDB269 | ggTTTTCggAggTCCgAgACg | (SEQ ID NO:31) |
| MDB283 | CTTggACCCCTAggTAAATgC | (SEQ ID NO:32) |
| MDB284 | gTACAAAACTTggACCCCTAgg | (SEQ ID NO:33) |

A fragment of 1068 bp (SEQ ID NO:34) was obtained, in which:

| 53–83: | 5' flanking region |
| 84–133: | target site deletion |
| 134–1055: | 3' flanking region |

Upon insertion of the T-DNA, 51 bp of the target site were deleted. Comparing the wild type locus sequence with the Rf3 locus revealed the presence of filler DNA at the Right border junction. The filler TCTCG sequence at the Right border is flanked by TCA at the 5'end and CGA at the 3'end. These triplets are also found at the breakpoint of the target site deletion and the T-DNA respectively. A search in more distal plant sequences revealed a possible origin of this filler DNA. The TCATCTCGCGA sequence is also located in the plant DNA at the 3'end of the target site deletion. It is the core sequence of two 13 bp identical repeats located 209 bp downstream of the breakpoint of the target site deletion.

The insertion region for RF-BN1 can be defined as comprising the left flanking region, the target site deletion and the right flanking region as follows:

| 1–836: | 5' flanking region (bp 46–881 of SEQ ID NO:24) |
| 837–887 | target site deletion (bp 84–133 of SEQ ID NO:34) |
| 888–2126 | 3' flanking region (bp 183–1457 of SEQ ID NO:30) |

4.3. Genetic Analysis of the Locus

The genetic stability of the inserts for the two events was checked by molecular and phenotypic analysis in the progeny plants over several generations.

Southern blot analyses of plants of the T0, T1 and T2 generations were compared for both event MS-BN1 and RF-BN1. The patterns obtained were found identical for each of the events in the different generations. This proves that the molecular configuration of the transgenes in both MS-BN1 and RF-BN1 containing plants was stable.

The MS-BN1 and RF-BN1 events displayed Mendelian segregation for their respective transgenes as single genetic loci in at least three subsequent generations indicating that the inserts are stable. On the basis of the above results MS-BN1 and MS-RF1 were identified as elite events.

4.4. Identification of the Flanking Sequences of MS-BN1 and RF-BN1 in WOSR

The flanking sequences of the elite events MS-BN1 and RF-BN1 in WOSR were determined using primers that were developed based on the flanking sequences of these events in spring oilseed rape.

MS-BN1 WOSR right (5') flanking sequence was determined using a T-DNA primer (SEQ ID NO:12) and a primer located in the MS-BN1 right border plant DNA:

VDS57: 5'-gCATgATCTgCT CgggATggC-3' (SEQ ID NO:35)

This yielded a fragment of 909 bp (SEQ ID NO:36) with a sequence essentially similar to the sequence of SEQ ID NO:13 (starting from nucleotide 98).

MS-BN1 WOSR left (3') flanking sequence was determined using a T-DNA primer (SEQ ID NO:17) and a primer located in the MS-BN1 left border plant DNA:

HCA68: 5'-CCATATAcgCCAgAgAggAC-3' (SEQ ID NO:37)

This yielded a fragment of 522 bp (SEQ ID NO:38) with a sequence essentially similar to the sequence of SEQ ID NO:18.

RF-BN1 WOSR right (5') flanking sequence was determined using a T-DNA primer (SEQ ID NO:12) and a primer located in the RF-BN1 right border plant DNA (SEQ ID NO:31). This yielded a fragment of 694 bp (SEQ ID NO:39) with a sequence essentially similar to the sequence of SEQ ID NO:24 (from nucleotide 293 to 980).

RF-BN WOSR left border sequence was determined using a T-DNA primer (SEQ ID NO:26) and a primer located in the RF-BN1 left border plant DNA (SEQ ID NO:29). This yielded a fragment of 1450 bp of which 1279 were sequenced (SEQ ID NO:40). This sequence was found to be essentially similar to the sequence of SEQ ID NO:30 (from nucleotide 141 to 1421).

Thus, left and right border sequences of the elite events MS-BN1 and RF-BN1 were confirmed to be essentially similar in SOSR and WOSR.

EXAMPLE 5

Development of Diagnostic Tools for Identity Control

The following protocols were developed to identify any WOSR plant material comprising the elite event MS-BN1.

5.1. MS-BN1 and RF-BN1 Elite Event Restriction Map Identification Protocol

WOSR plants containing the elite event MS-BN1 can be identified by Southern blotting using essentially the same procedure as described in Example 4.1. Thus WOSR genomic DNA is 1) digested with at least two, preferably at least 3, particularly with at least 4, more particularly with all of the following restriction enzymes: EcoRI, EcoRV, NdeI, HpaI, AflIII 2) transferred to nylon membranes and 3) hybridized with the 3942 bp HindIII fragment of plasmid pTHW107. If, with respect to at least two of the restriction enzymes used, DNA fragments are identified with the same length as those listed in Table 3 of Example 4.1.1., the WOSR plant is determined to harbor elite event MS-BN1.

WOSR plants containing the elite event RF-BN1 can be identified by Southern blotting using essentially the same procedure as described in Example 4.1. Thus WOSR genomic DNA is 1) digested with at least two, preferably at least three, most preferably with all of the following restriction enzymes: BamHI, EcoRI, EcoRV, HindIII 2) transferred to nylon membranes and 3) hybridized with the 2182 bp HpaI fragment of plasmid pTHW118. If, with respect to at least two of the restriction enzymes used, DNA fragments are identified with the same length as those listed in Table 4 in Example 4.1.2., the WOSR plant is determined to harbor elite event RF-BN1.

5.2. MS-BN1 and RF-BN1 Elite Event PCR Identification Protocol

A test run, with all appropriate controls, has to be performed before attempting to screen unknowns. The presented protocol might require optimization for components that may differ between labs (template DNA preparation, Taq DNA polymerase, quality of the primers, dNTP's, thermocyler, etc.).

Amplification of the endogenous sequence plays a key role in the protocol. One has to attain PCR and thermocycling conditions that amplify equimolar quantities of both the endogenous and transgenic sequence in a known transgenic genomic DNA template. Whenever the targeted endogenous fragment is not amplified or whenever the targeted sequences are not amplified with the same ethidium bromide staining intensities, as judged by agarose gel electrophoresis, optimization of the PCR conditions may be required.

5.2.1. Template DNA

Template DNA is prepared from a leaf punch or a single seed according to Edwards et al. ((1991) Nucl. Acid Res. 19:1349). When using DNA prepared with other methods, a test run utilizing different amounts of template should be done. Usually 50 ng of genomic template DNA yields the best results.

5.2.2. Assigned Positive and Negative Controls

The following positive and negative controls should be included in a PCR run:

Master Mix control (DNA negative control). This is a PCR in which no DNA is added to the reaction. When the expected result, no PCR products, is observed this indicates that the PCR cocktail was not contaminated with target DNA.

A DNA positive control (genomic DNA sample known to contain the transgenic sequences). Successful amplification of this positive control demonstrates that the PCR was run under conditions that allow for the amplification of target sequences.

A wildtype DNA control. This is a PCR in which the template DNA provided is genomic DNA prepared from a non-transgenic plant. When the expected result, no amplification of the transgene PCR product but amplification of the endogenous PCR product, is observed this indicates that there is no detectable transgene background amplification in a genomic DNA sample.

5.2.3. Primers

The following primers, which specifically recognize the transgene and a flanking sequence of MS-BN1 are used:

BNA01: 5'-gCT.Tgg.ACT.ATA.ATA.CCT.gAC-3' (SEQ ID NO:12)
(MDB201) (target: transgene)
BNA02: 5'-TgA.CAC.TTT.gAg.CCA.CTC.g-3' (SEQ ID NO:19)
(VDS51) (target: plant DNA)

To identify plant material comprising RF-BN1, the following primers, which specifically recognize the transgene and a flanking sequence of RF-BN1 are used:

BNA03: 5'-TCA.TCT.ACg.gCA.ATg.TAC.CAgC-3' (SEQ ID NO:23)
(MDB193) (target: transgene)
BNA04: 5'-Tgg.ACC.CCT.Agg.TAA.ATg.CC-3' (SEQ ID NO:41)
(MDB268) (target: plant DNA)

Primers targeting an endogenous sequence are always included in the PCR cocktail. These primers serve as an internal control in unknown samples and in the DNA positive control. A positive result with the endogenous primer-pair demonstrates that there is ample DNA of adequate quality in the genomic DNA preparation for a PCR product to be generated. The endogenous primers used are:

BNA05: 5'-AACgAgTgTCAgCTAgACCAgC-3' (SEQ ID NO:42)
BNA06: 5'-CgCAgTTCTgTgAACATCgACC-3' (SEQ ID NO:43)

5.2.4. Amplified Fragments

The expected amplified fragments in the PCR reaction are:

For primer pair BNA05-BNA06: 394 bp (endogenous control)
For primer pair BNA01-BNA02: 280 bp (MS-BN1 Elite Event)
For primer pair BNA03-BNA04: 215 bp (RF-BN1 Elite Event)

5.2.5. PCR Conditions

The PCR mix for 50 µl reactions contains:

5 µl template DNA
5 µl 10× Amplification Buffer (supplied with Taq polymerase)
1 µl 10 mM dNTP's
1 µl BNA01 (MS-BN1) or BNA03 (RF-BN1)(10 pmoles/µl)
1 µl BNA02 (RF-BN1) or BNA04 (RF-BN1) (10 pmoles/µl)
0.5 µl BNA05 (10 pmoles/µl)
0.5 µl BNA06 (10 pmoles/µl)
0.2 µl Taq DNA polymerase (5 units/µl)
water up to 50 µl The thermocycling profile to be followed for optimal results is the following:

4 min. at 95° C.

Followed by:
1 min. at 95° C.
1 min. at 57° C.
2 min. at 72° C.
For 5 cycles

Followed by:
30 sec. at 92° C.
30 sec. at 57° C.
1 min. at 72° C.
For 22 to 25 cycles Followed by:
5 minutes at 72° C.

5.2.6. Agarose Gel Analysis

Between 10 and 20 µl of the PCR samples should be applied on a 1.5% agarose gel (Tris-borate buffer) with an appropriate molecular weight marker (e.g. 100 bp ladder PHARMACIA).

5.2.7. Validation of the Results

Data from transgenic plant DNA samples within a single PCR run and a single PCR cocktail should not be acceptable unless 1) the DNA positive control shows the expected PCR products (transgenic and endogenous fragments), 2) the DNA negative control is negative for PCR amplification (no fragments) and 3) the wild-type DNA control shows the expected result (endogenous fragment amplification).

Lanes showing visible amounts of the transgenic and endogenous PCR products of the expected sizes, indicate that the corresponding plant from which the genomic template DNA was prepared, has inherited the MS-BN1 and/or RF-BN1 elite event. Lanes not showing visible amounts of either of the transgenic PCR products and showing visible amounts of the endogenous PCR product, indicate that the corresponding plant from which the genomic template DNA was prepared, does not comprise the elite event. Lanes not showing visible amounts of the endogenous and transgenic PCR products, indicate that the quality and/or quantity of the genomic DNA didn't allow for a PCR product to be generated. These plants cannot be scored. The genomic DNA preparation should be repeated and a new PCR run, with the appropriate controls, has to be performed.

5.2.8. Use of Discriminating PCR to Identify MS-BN1 and RF-BN1

WOSR leaf material from plants comprising either MS-BN1, RF-BN1 or another transgenic event was tested according to the above-described protocol. Samples from WOSR wild-type were taken as negative controls.

Figure 4:
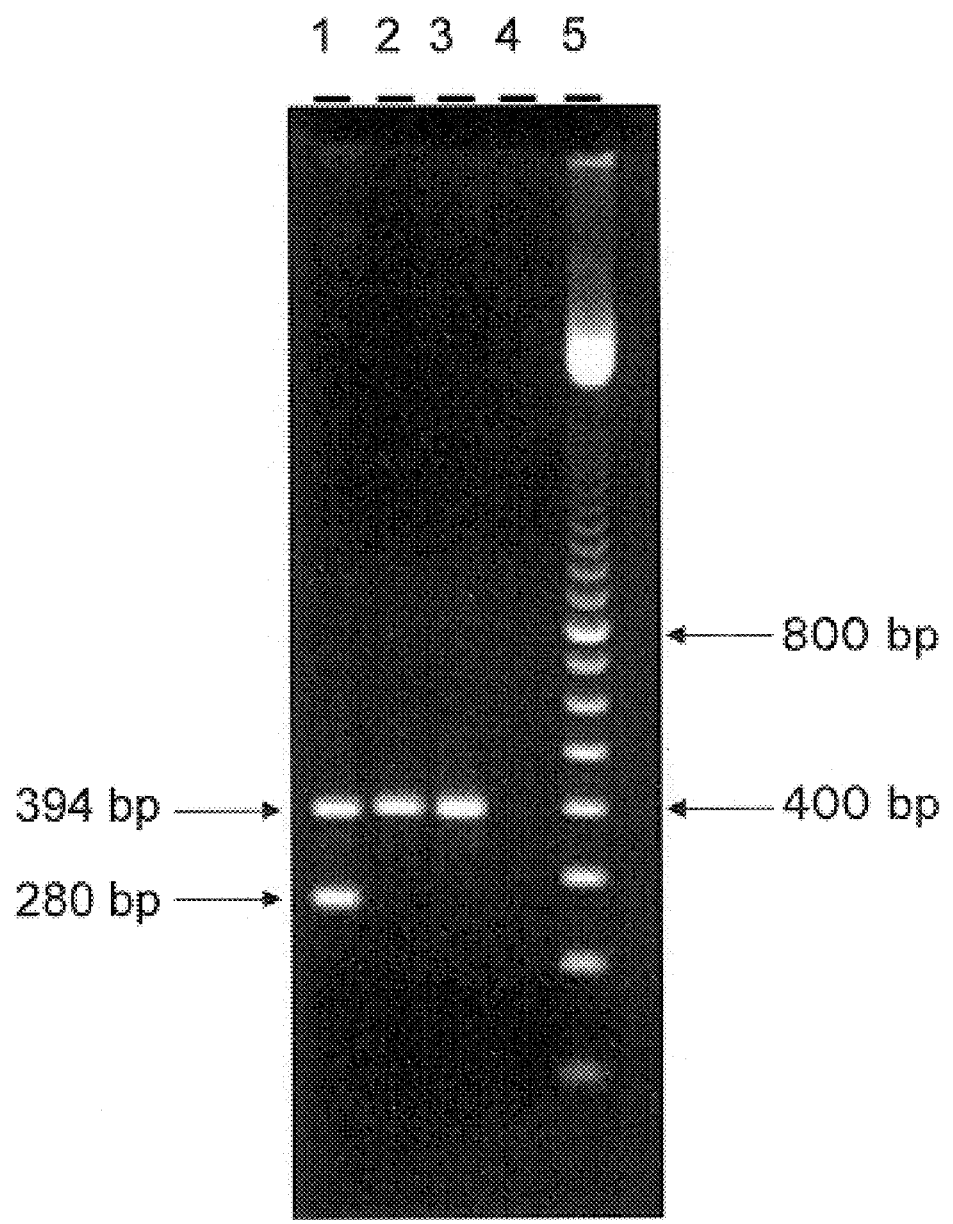
FIG. 4 depicts PCR analysis of different lines using the MS-BN1 PCR identification protocol. Loading sequence of the gel: lane 1, DNA sample from an OSR plant comprising the transgenic event MS-BN1, lane 2, DNA sample from an OSR plant comprising another transgenic event, lane 3, DNA from wild-type OSR, lane 4, negative control (water), lane 5, molecular weight marker (100 bp ladder).
Figure 5:
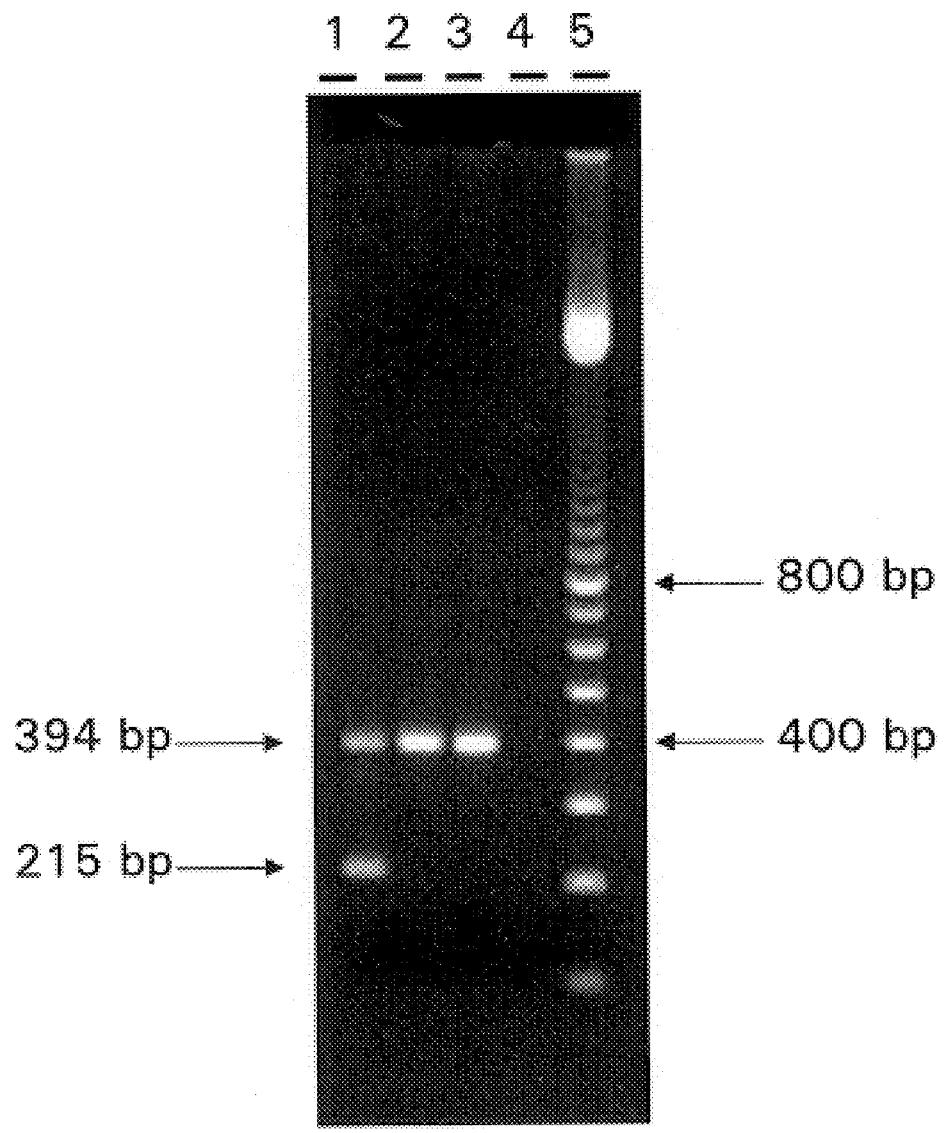
FIG. 5 depicts PCR analysis of different lines using the RF-BN1 PCR identification protocol. Loading sequence of the gel: lane 1, DNA sample from an OSR plant comprising the transgenic event RF-BN1, lane 2, DNA sample from an OSR plant comprising another transgenic event, lane 3, DNA from wild-type OSR, lane 4, negative control (water), lane 5, molecular weight marker (100 bp ladder).

The results of the PCR analysis are illustrated in FIGS. 4 and 5.

FIG. 4 illustrates the result obtained with the elite event PCR identification protocol for MS-BN1 on two WOSR samples (lane 1 and 2). Lane 1 is recognized to contain the elite event as the 280 bp band is detected while the sample in lane 2 does not comprise MS-BN1.

FIG. 5 illustrates the result obtained with the elite event PCR identification protocol for RF-BN1 on two WOSR samples (lane 1 and 2). Lane 1 is recognized to contain the elite event as the 215 bp band is detected while the sample in lane 2 does not comprise RF-BN1.

EXAMPLE 6

Production of Hybrid Seed Using MS-BN1 and RF-BN1 in WOSR

WOSR Plants comprising MS-BN1 which were male sterile were crossed with WOSR plants homozygous for RF-BN1. Hybrid seed was collected from MS-BN1 and deposited at the ATCC under ATCC accession number PTA-730.

This hybrid seed was replanted in the field. Plants were found to be 100% fertile and displaying optimal agronomic characteristics. Hybrid plants comprised either both the MS-BN1 and RF-BN1 or the RF-BN-1 event alone.

EXAMPLE 7

Introduction of MS-BN1 and RF-BN1 into Preferred Cultivars of WOSR

Elite events MS-BN1 and RF-BN1 were introduced by repeated backcrossing of plants comprising event MS-BN1 or RF-BN1, respectively, into a number of agriculturally important WOSR cultivars.

It was observed that the introgression of the elite events into these cultivars did not significantly influence any of the desirable phenotypic or agronomic characteristics of these cultivars (no linkage drag) while expression of the transgene, as determined by glufosinate tolerance, meets commercially acceptable levels. This confirms the status of event MS-BN1 and RF-BN1 as elite events.

As used in the claims below, unless otherwise clearly indicated, the term "plant" is intended to encompass plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts.

Seed comprising elite event MS-BN1 and elite event RF-BN1 or elite event RF-BN1 alone was deposited at the American Tissue Culture Collection under accession number: PTA-730.

What is claimed is:

1. A transgenic winter oilseed rape (WOSR) plant, seed, plant cell or tissue, which is characterized in that the genomic DNA of said plant, seed, plant cell or tissue yields a DNA fragment of between 260 and 300 bp when analyzed according to the MS-BN1 Elite Event PCR identification protocol using two primers having the nucleotide sequence of SEQ ID NO: 12 and SEQ ID NO: 19 respectively.

2. The plant, seed, plant cell or tissue of claim 1, characterized in that the genomic DNA of said plant, seed, plant cell or tissue yields, when analyzed according to the MS-BN1 Elite Event Restriction map identification protocol, at least three restriction fragments or pairs of restriction fragments selected from the group consisting of:
   i) one set of EcoRI fragments, one with a length of between 2140 and 2450 bp, preferably of about 2266 bp, and one with a length of more than 14 kbp;
   ii) one set of EcoRV fragments wherein one has a length of between 1159 and 1700 bp, preferably of about 1.4 kbp and the other has a length of more than 14 kbp;
   iii) one set of HpaI fragments, one with a length of between 1986 and 2140 bp, preferably with a length of about 1990 bp, and one with a length of between 2140 and 2450 bp, preferably of about 2229 bp;
   iv) one set of AflIII fragments, one with a length of between 514 and 805 bp, preferably with a length of about 522 bp, and one with a length of between 2140 and 2450 bp, preferably about 2250 bp, and one with a length of between 2450 and 2838 bp, preferably of about 2477 bp; and
   v) one set of NdeI fragments, both with a length of between 5077 and 14057 bp, preferably one of about 6500 bp, and one with a length of about 10 kbp;
wherein each of the restriction fragments hybridizes under standard stringency conditions with the 3942 bp fragment comprising the PTA29-barnase sequence obtained by HindIII digestion of the plasmid pTHW107 having the sequence of SEQ ID NO: 1.

3. The plant, seed, plant cells or tissue of claim 2, wherein the genomic DNA of said plant, seed, plant cells or tissue yields, when analyzed according to the MS-BN1 Elite Event Restriction map identification protocol, at least four sets of restriction fragments selected from said group.

4. The plant, seed, plant cells or tissue of claim 2, wherein the genomic DNA of said plant, seed, plant cells or tissue yields, when analyzed according to the MS-BN1 Elite Event Restriction map identification protocol, at least five sets of restriction fragments selected from said group.

5. The plant, seed, plant cell or tissue of claim 1, characterized in that the genomic DNA yields a DNA fragment of about 280 bp when analyzed according to the MS-BN1 Elite Event PCR identification protocol using two primers having the nucleotide sequence of SEQ ID NO: 12 and SEQ ID NO: 19 respectively.

6. A method for producing hybrid WOSR seed, said method comprising
   a) crossing a transgenic, male-sterile WOSR plant, characterized in that the genomic DNA of said WOSR plant yields a DNA fragment of between 260 and 300 bp when analyzed according to the MS-BN1 Elite Event PCR identification protocol using two primers having the nucleotide sequence of SEQ ID NO: 12 and SEQ ID NO: 19 respectively, with a fertility restorer WOSR plant, comprising, stably integrated into its genome, a fertility-restorer gene comprising:
      a DNA encoding a ribonuclease inhibitor; and
      a constitutive promoter, wherein said DNA is in the same transcriptional unit and is under the control of said constitutive promoter; and
   b) harvesting said hybrid seed from said male sterile WOSR plant.

7. The method of claim 6, wherein said fertility restorer plant is further characterized in that the genomic DNA of said restorer plant yields a DNA fragment of between 195 and 235, using the RF-BN1 Elite Event Polymerase Chain reaction identification protocol with two primers having the nucleotide sequence of SEQ ID NO: 23 and SEQ ID NO: 41 respectively.

8. A hybrid seed of WOSR produced according to the method of claim 6 or 7.

9. A process for producing a transgenic winter oilseed rape (WOSR) plant cell or plant comprising elite event MS-BN1, said process comprising inserting a recombinant DNA molecule encoding a barnase enzyme into a part of the chromosomal DNA of a WOSR cell, said part of the chromosomal DNA of a WOSR cell characterized by the sequence of SEQ ID NO: 22, and regenerating a WOSR plant from the transformed WOSR cell.

10. A transgenic WOSR plant cell or plant produced by the method of claim 9.

* * * * *

UNITED STATES PATENT AND TRADEMARK OFFICE
CERTIFICATE OF CORRECTION

PATENT NO.         : 6,563,026 B2
APPLICATION NO. : 09/733151
DATED                 : May 13, 2003
INVENTOR(S)       : De Both et al.

It is certified that error appears in the above-identified patent and that said Letters Patent is hereby corrected as shown below:

Cover page, ABSTRACT, line 2, please delete the word "wherein";

Cover page, ABSTRACT, line 6, please replace the word "wherein" with the words --characterized by--;

Cover page, ABSTRACT, line 8, please replace the word "wherein" with the words --characterized by--;

Column 1, line 18, please replace the word "wherein" with the words --characterized by--;

Column 1, line 20, please replace the word "wherein" with the words --characterized by--;

Column 3, line 12, please replace the word "wherein" with the words --characterized by--;

Column 4, line 8, please replace the word "wherein" with the words --characterized by--;

Column 4, line 27, please replace the word "wherein" with the words --characterized by--;

Column 4, line 41, please replace the word "wherein" with the words --characterized by--;

Column 4, line 45, please replace the word "wherein" with the words --characterized by--;

Column 5, line 17, please delete the words "wherein it is";

UNITED STATES PATENT AND TRADEMARK OFFICE
CERTIFICATE OF CORRECTION

| | |
|---|---|
| PATENT NO. | : 6,563,026 B2 |
| APPLICATION NO. | : 09/733151 |
| DATED | : May 13, 2003 |
| INVENTOR(S) | : De Both et al. |

It is certified that error appears in the above-identified patent and that said Letters Patent is hereby corrected as shown below:

Column 5, line 26, please replace the word "wherein" with the words --characterized by--;

Column 6, line 16, please replace the word "wherein" with the words --characterized by--;

Column 6, line 18, please replace the word "wherein" with the words --characterized by--;

Column 6, line 24, please replace the word "wherein" with the words --characterized by--;

Column 6, line 26, please replace the word "wherein" with the words --characterized by--;

Column 6, line 42, please replace the word "wherein" with the word --having--;

Column 6, line 45, please replace the word "wherein" with the word --having--;

Column 6, line 50, please replace the word "wherein" with the word --having--;

Column 6, line 57, please replace the word "wherein" with the word --having--;

Column 10, line 60, please replace the word "wherein" with the words --characterized by--;

Column 11, line 40, please replace the word "wherein" with the words --characterized by--;

Column 11, line 59, please replace the word "wherein" with the words --characterized by--;

UNITED STATES PATENT AND TRADEMARK OFFICE
CERTIFICATE OF CORRECTION

PATENT NO. : 6,563,026 B2
APPLICATION NO. : 09/733151
DATED : May 13, 2003
INVENTOR(S) : De Both et al.

It is certified that error appears in the above-identified patent and that said Letters Patent is hereby corrected as shown below:

Column 13, line 66, please delete the words "wherein the";

Column 15, line 7, please replace the word "wherein" with the words --characterized by--;

Column 15, line. 65, please replace the word "wherein" with the words

--characterized by--;

Column 16, line 18, please replace the word "wherein" with the words

--characterized by--;

Column 16, line 25, please replace the word "wherein" with the words

--characterized by--;

Column 16, line 35, please replace the word "wherein" with the words

--characterized by--;

Column 23, line 13, please replace the word "wherein" with the words

--characterized by--

Signed and Sealed this

Ninth Day of January, 2007

JON W. DUDAS
*Director of the United States Patent and Trademark Office*

SEQUENCE LISTING

```
<160> NUMBER OF SEQ ID NOS:   43

<210> SEQ ID NO 1
<211> LENGTH: 4946
<212> TYPE: DNA
<213> ORGANISM: Artificial Sequence
<220> FEATURE:
<221> NAME/KEY: misc_feature
<222> LOCATION: (1)..(4946)
<223> OTHER INFORMATION: Plasmid pTHW107

<400> SEQUENCE: 1
aattacaacg gtatatatcc tgccagtact cggccgtcga actcggccgt cgagtacatg      60
gtcgataaga aaggcaatt  tgtagatgtt aattcccatc ttgaaagaaa tatagtttaa     120
atatttattg ataaaataac aagtcaggta ttatagtcca agcaaaaaca taaatttatt     180
gatgcaagtt taaattcaga aatatttcaa taactgatta tatcagctgg tacattgccg     240
tagatgaaag actgagtgcg atattatgtg taatacataa attgatgata tagctagctt     300
agctcatcgg gggatcctag acgcgtgaga tcagatctcg gtgacgggca ggaccggacg     360
gggcggtacc ggcaggctga agtccagctg ccagaaaccc acgtcatgcc agttcccgtg     420
cttgaagccg gccgcccgca gcatgccgcg gggggcatat ccgagcgcct cgtgcatgcg     480
cacgctcggg tcgttgggca gcccgatgac agcgaccacg ctcttgaagc cctgtgcctc     540
cagggacttc agcaggtggg tgtagagcgt ggagcccagt cccgtccgct ggtggcgggg     600
ggagacgtac acggtcgact cggccgtcca gtcgtaggcg ttgcgtgcct tccaggggcc     660
cgcgtaggcg atgccggcga cctcgccgtc cacctcggcg acgagccagg gatagcgctc     720
```

```
ccgcagacgg acgaggtcgt ccgtccactc ctgcggttcc tgcggctcgg tacggaagtt    780
gaccgtgctt gtctcgatgt agtggttgac gatggtgcag accgccggca tgtccgcctc    840
ggtggcacgg cggatgtcgg ccgggcgtcg ttctgggtcc attgttcttc tttactcttt    900
gtgtgactga ggtttggtct agtgctttgg tcatctatat ataatgataa caacaatgag    960
aacaagcttt ggagtgatcg gagggtctag gatacatgag attcaagtgg actaggatct   1020
acaccgttgg attttgagtg tggatatgtg tgaggttaat tttacttggt aacggccaca   1080
aaggcctaag gagaggtgtt gagacccta tcggcttgaa ccgctggaat aatgccacgt    1140
ggaagataat tccatgaatc ttatcgttat ctatgagtga aattgtgtga tggtggagtg   1200
gtgcttgctc atttacttg cctggtggac ttggcccttt ccttatgggg aatttatatt    1260
ttacttacta tagagctttc atacctttt tttaccttgg atttagttaa tatataatgg    1320
tatgattcat gaataaaaat gggaattttt tgaatttgta ctgctaaatg cataagatta   1380
ggtgaaactg tggaatatat attttttttca tttaaaagca aaatttgcct tttactagaa   1440
ttataaatat agaaaatat ataacattca aataaaaatg aaaataagaa cttcaaaaa    1500
acagaactat gtttaatgtg taaagattag tcgcacatca agtcatctgt tacaatatgt   1560
tacaacaagt cataagccca acaaagttag cacgtctaaa taaactaaag agtccacgaa   1620
aatattacaa atcataagcc caacaaagtt attgatcaaa aaaaaaaaac gcccaacaaa   1680
gctaaacaaa gtccaaaaaa aacttctcaa gtctccatct tcctttatga acattgaaaa   1740
ctatacacaa aacaagtcag ataaatctct ttctgggcct gtcttcccaa cctcctacat   1800
cacttcccta tcggattgaa tgttttactt gtaccttttc cgttgcaatg atattgatag   1860
tatgtttgtg aaaactaata gggttaacaa tcgaagtcat ggaatatgga tttggtccaa   1920
gattttccga gagcttttcta gtagaaagcc catcaccaga aatttactag taaaataaat   1980
caccaattag gtttcttatt atgtgccaaa ttcaatataa ttatagagga tatttcaaat   2040
gaaaacgtat gaatgttatt agtaaatggt caggtaagac attaaaaaaa tcctacgtca   2100
gatattcaac tttaaaaatt cgatcagtgt ggaattgtac aaaaatttgg gatctactat   2160
atatataaa tgctttacaa cacttggatt ttttttgga ggctggaatt tttaatctac    2220
atatttgttt tggccatgca ccaactcatt gtttagtgta atactttgat tttgtcaaat   2280
atatgtgttc gtgtatattt gtataagaat ttctttgacc atatacacac acacatatat   2340
atatatatat atatattata tatcatgcac ttttaattga aaaataata tatatatata   2400
tagtgcattt tttctaacaa ccatatatgt tgcgattgat ctgcaaaaat actgctagag   2460
taatgaaaaa tataatctat tgctgaaatt atctcagatg ttaagatttt cttaaagtaa   2520
attctttcaa attttagcta aaagtcttgt aataactaaa gaataataca caatctcgac   2580
cacggaaaaa aaacacataa taaatttgaa tttcgaccgc ggtacccgga attcgagctc   2640
ggtacccggg gatcttcccg atctagtaac atagatgaca ccgcgcgcga taatttatcc   2700
tagtttgcgc gctatatttt gttttctatc gcgtattaaa tgtataattg cgggactcta   2760
atcataaaaa cccatctcat aaataacgtc atgcattaca tgttaattat tacatgctta   2820
acgtaattca acagaaatta tatgataatc atcgcaagac cggcaacagg attcaatctt   2880
aagaaacttt attgccaaat gtttgaacga tctgcttcgg atcctctaga gccggaaagt   2940
gaaattgacc gatcagagtt tgaagaaaaa tttattacac actttatgta aagctgaaaa   3000
aaacggcctc cgcaggaagc cgttttttc gttatctgat ttttgtaaag gtctgataat   3060
```

```
ggtccgttgt tttgtaaatc agccagtcgc ttgagtaaag aatccggtct gaatttctga   3120
agcctgatgt atagttaata tccgcttcac gccatgttcg tccgcttttg cccgggagtt   3180
tgccttccct gtttgagaag atgtctccgc cgatgctttt cccgagcg acgtctgcaa    3240 ggttcccttt tgatgccacc cagccgaggg cttgtgcttc tgattttgta atgtaattat   3300
caggtagctt atgatatgtc tgaagataat ccgcaacccc gtcaaacgtg ttgataaccg   3360
gtaccatggt agctaatttc tttaagtaaa actttgatt tgagtgatga tgttgtactg    3420
ttacacttgc accacaaggg catatataga gcacaagaca tacacaacaa cttgcaaaac   3480
taacttttgt tggagcattt cgaggaaaat ggggagtagc aggctaatct gagggtaaca   3540
ttaaggtttc atgtattaat ttgttgcaaa catggactta gtgtgaggaa aaagtaccaa   3600
aattttgtct caccctgatt tcagttatgg aaattacatt atgaagctgt gctagagaag   3660
atgtttattc tagtccagcc acccacctta tgcaagtctg cttttagctt gattcaaaaa   3720
ctgatttaat ttacattgct aaatgtgcat acttcgagcc tatgtcgctt taattcgagt   3780
aggatgtata tattagtaca taaaaaatca tgtttgaatc atctttcata aagtgacaag   3840
tcaattgtcc cttcttgttt ggcactatat tcaatctgtt aatgcaaatt atccagttat   3900
acttagctag atatccaatt ttgaataaaa atagctcttg attagtaaac cggatagtga   3960
caaagtcaca tatccatcaa acttctggtg ctcgtggcta agttctgatc gacatggggt   4020
taaaatttaa attgggacac ataaatagcc tatttgtgca aatctcccca tcgaaaatga   4080
cagattgtta catggaaaac aaaaagtcct ctgatagaag tcgcaaagta tcacaatttt   4140
ctatcgagag atagattgaa agaagtgcag ggaagcggtt aactggaaca taacacaatg   4200
tctaaattaa ttgcattcgc taaccaaaaa gtgtattact ctctccggtc cacaataagt   4260 tatttttttgg ccctttttt atggtccaaa ataagtgagt tttttagatt tcaaaaatga   4320
tttaattatt ttttactac agtgcccttg gagtaaatgg tgttggagta tgtgttagaa    4380
atgtttatgt gaagaaatag taaggttaa tatgatcaat ttcattgcta tttaatgtta    4440
aaatgtgaat ttcttaatct gtgtgaaaac aaccaaaaaa tcacttattg tggaccggag   4500
aaagtatata aatatatatt tggaagcgac taaaaataaa ctttttctcat attatacgaa   4560 cctaaaaaca gcatatggta gtttctaggg aatctaaatc actaaaatta ataaaagaag   4620
caacaagtat caatacatat gatttacacc gtcaaacacg aaattcgtaa atatttaata   4680
taataaagaa ttaatccaaa tagcctccca ccctataact taaactaaaa ataaccagcg   4740
aatgtatatt atatgcataa tttatatatt aaatgtgtat aatcatgtat aatcaatgta   4800
taatctatgt atatggttag aaaaagtaaa caattaaat agccggctat ttgtgtaaaa    4860
atccctaata taatcgcgac ggatccccgg gaattccggg gaagcttaga tccatggagc   4920
catttacaat tgaatatatc ctgccg                                        4946

<210> SEQ ID NO 2
<211> LENGTH: 4832
<212> TYPE: DNA
<213> ORGANISM: Artificial Sequence
<220> FEATURE:
<221> NAME/KEY: misc_feature
<222> LOCATION: (1)..(4832)
<223> OTHER INFORMATION: Plasmid pTHW118

<400> SEQUENCE: 2
aattacaacg gtatatatcc tgccagtact cggccgtcga actcggccgt cgagtacatg     60
gtcgataaga aaaggcaatt tgtagatgtt aattcccatc ttgaaagaaa tatagtttaa   120
```

```
atatttattg ataaaataac aagtcaggta ttatagtcca agcaaaaaca taaatttatt      180
gatgcaagtt taaattcaga aatatttcaa taactgatta tatcagctgg tacattgccg      240
tagatgaaag actgagtgcg atattatgtg taatacataa attgatgata tagctagctt      300
agctcatcgg gggatcctag acgcgtgaga tcagatctcg gtgacgggca ggaccggacg      360
gggcggtacc ggcaggctga agtccagctg ccagaaaccc acgtcatgcc agttcccgtg      420
cttgaagccg gccgcccgca gcatgccgcg ggggcatat ccgagcgcct cgtgcatgcg       480
cacgctcggg tcgttgggca gcccgatgac agcgaccacg ctcttgaagc cctgtgcctc      540
cagggacttc agcaggtggg tgtagagcgt ggagcccagt cccgtccgct ggtggcgggg      600
ggagacgtac acggtcgact cggccgtcca gtcgtaggcg ttgcgtgcct tccaggggcc      660
cgcgtaggcg atgccggcga cctcgccgtc cacctcggcg acgagccagg atagcgctc      720 ccgcagacgg acgaggtcgt ccgtccactc ctgcggttcc tgcggctcgg tacggaagtt      780
gaccgtgctt gtctcgatgt agtggttgac gatggtgcag accgccggca tgtccgcctc      840
ggtggcacgg cggatgtcgg ccgggcgtcg ttctgggtcc attgttcttc tttactctt       900 gtgtgactga ggtttggtct agtgctttgg tcatctatat ataatgataa caacaatgag      960
aacaagcttt ggagtgatcg gagggtctag gatacatgag attcaagtgg actaggatct      1020
acaccgttgg attttgagtg tggatatgtg tgaggttaat tttacttggt aacggccaca      1080
aaggcctaag gagaggtgtt gagaccctta tcggcttgaa ccgctggaat aatgccacgt      1140
ggaagataat tccatgaatc ttatcgttat ctatgagtga aattgtgtga tggtggagtg      1200
gtgcttgctc atttacttg cctggtggac ttggcccttt ccttatgggg aatttatatt       1260
ttacttacta tagagctttc ataccttttt tttaccttgg atttagttaa tatataatgg      1320
tatgattcat gaataaaaat gggaaatttt tgaatttgta ctgctaaatg cataagatta      1380
ggtgaaactg tggaatatat attttttca tttaaaagca aaatttgcct tttactagaa       1440
ttataaatat agaaaaatat ataacattca aataaaaatg aaaataagaa ctttcaaaaa      1500
acagaactat gtttaatgtg taaagattag tcgcacatca agtcatctgt tacaatatgt      1560
tacaacaagt cataagccca acaaagttag cacgtctaaa taaactaaag agtcccacgaa      1620 aatattacaa atcataagcc caacaaagtt attgatcaaa aaaaaaaaac gcccaacaaa      1680
gctaaacaaa gtccaaaaaa aacttctcaa gtctccatct tcctttatga acattgaaaa      1740
ctatacacaa aacaagtcag ataaatctct ttctgggcct gtcttcccaa cctcctacat      1800
cacttcccta tcggattgaa tgttttactt gtaccttttc cgttgcaatg atattgatag      1860
tatgtttgtg aaaactaata gggttaacaa tcgaagtcat ggaatatgga tttggtccaa      1920
gattttccga gagctttcta gtagaaagcc catcaccaga aatttactag taaaataaat      1980
caccaattag gtttcttatt atgtgccaaa ttcaatataa ttatagagga tatttcaaat      2040
gaaaacgtat gaatgttatt agtaaatggt caggtaagac attaaaaaaa tcctacgtca      2100
gatattcaac tttaaaaatt cgatcagtgt ggaattgtac aaaaatttgg gatctactat      2160
atatatataa tgctttacaa cacttggatt ttttttgga ggctggaatt tttaatctac       2220
atatttgttt tggccatgca ccaactcatt gtttagtgta atactttgat tttgtcaaat      2280
atatgtgttc gtgtatattt gtataagaat ttctttgacc atatacacac acacatatat      2340
atatatatat atatattata tatcatgcac ttttaattga aaaataaata tatatatata      2400
tagtgcattt tttctaacaa ccatatatgt tgcgattgat ctgcaaaaat actgctagag      2460
```

```
taatgaaaaa tataatctat tgctgaaatt atctcagatg ttaagatttt cttaaagtaa    2520
attctttcaa attttagcta aaagtcttgt aataactaaa gaataataca caatctcgac    2580
cacggaaaaa aaacacataa taaatttgaa tttcgaccgc ggtacccgga attcgagctc    2640
ggtacccggg gatcttcccg atctagtaac atagatgaca ccgcgcgcga taatttatcc    2700
tagtttgcgc gctatatttt gttttctatc gcgtattaaa tgtataattg cgggactcta    2760
atcataaaaa cccatctcat aaataacgtc atgcattaca tgttaattat tacatgctta    2820
acgtaattca acagaaatta tatgataatc atcgcaagac cggcaacagg attcaatctt    2880
aagaaacttt attgccaaat gtttgaacga tctgcttcgg atcctctaga ccaagcttgc    2940
gggtttgtgt ttccatattg ttcatctccc attgatcgta ttaagaaagt atgatggtga    3000
tgtcgcagcc ttccgctttc gcttcacgga aaacctgaag cacactctcg gcgccatttt    3060
cagtcagctg cttgctttgt tcaaactgcc tccattccaa aacgagcggg tactccaccc    3120
atccggtcag acaatcccat aaagcgtcca ggttttcacc gtagtattcc ggaagggcaa    3180
gctccttttt caatgtctgg tggaggtcgc tgatacttct gatttgttcc ccgttaatga    3240 ctgcttttt catcggtagc taatttcttt aagtaaaaac tttgatttga gtgatgatgt    3300
tgtactgtta cacttgcacc acaagggcat atatagagca caagacatac acaacaactt    3360
gcaaaactaa cttttgttgg agcatttcga ggaaaatggg gagtagcagg ctaatctgag    3420
ggtaacatta aggtttcatg tattaatttg ttgcaaacat ggacttagtg tgaggaaaaa    3480
gtaccaaaat tttgtctcac cctgatttca gttatggaaa ttacattatg aagctgtgct    3540
agagaagatg tttattctag tccagccacc caccttatgc aagtctgctt ttagcttgat    3600
tcaaaaactg atttaattta cattgctaaa tgtgcatact tcgagcctat gtcgctttaa    3660
ttcgagtagg atgtatatat tagtacataa aaaatcatgt ttgaatcatc tttcataaag    3720
tgacaagtca attgtccctt cttgtttggc actatattca atctgttaat gcaaattatc    3780
cagttatact tagctagata tccaattttg aataaaaata gctcttgatt agtaaaccgg    3840
atagtgacaa agtcacatat ccatcaaact tctggtgctc gtggctaagt tctgatcgac    3900
atggggttaa aatttaaatt gggacacata aatagcctat tgtgcaaat ctccccatcg    3960 aaaatgacaa attgttacat ggaaaacaaa aagtcctctg atagaagtcg caaagtatca    4020
caattttcta tcgagagata gattgaaaga agtgcaggga agcggttaac tggaacataa    4080
cacaatgtct aaattaattg cattcgctaa ccaaaaagtg tattactctc tccggtccac    4140
aataagttat ttttggccc ttttttatg gtccaaaata agtgagtttt ttagatttca    4200
aaaatgattt aattatttt ttactacagt gcccttggag taaatggtgt tggagtatgt    4260
gttagaaatg tttatgtgaa gaaatagtaa aggttaatat gatcaatttc attgctatt    4320 aatgttaaaa tgtgaatttc ttaatctgtg tgaaaacacc aaaaaatcac ttattgtgga    4380
ccggagaaag tatataaata tatatttgga agcgactaaa aataaacttt tctcatatta    4440
tacgaaccta aaaacagcat atggtagttt ctagggaatc taaatcacta aaattaataa    4500
aagaagcaac aagtatcaat acatatgatt tacaccgtca aacacgaaat tcgtaaatat    4560
ttaatataat aaagaattaa tccaaatagc ctcccaccct atkacttaaa ctaaaaataa    4620
ccagcgaatg tatattatat gcataattta tatattaaat gtgtataatc atgtataatc    4680
aatgtataat ctatgtatat ggttagaaaa agtaaacaat taatatagcc ggctatttgt    4740
gtaaaaatcc ctaatataat cgcgacggat ccccgggaat tccggggaag cttagatcca    4800
tggagccatt tacaattgaa tatatcctgc cg                                  4832
```

<210> SEQ ID NO 3
<211> LENGTH: 60
<212> TYPE: DNA
<213> ORGANISM: Artificial Sequence
<220> FEATURE:
<221> NAME/KEY: misc_feature
<222> LOCATION: (1)..(60)
<223> OTHER INFORMATION: Primer 248

<400> SEQUENCE: 3
catgccctga cccaggctaa gtattttaac tttaaccact ttgctccgac agtcccattg    60

<210> SEQ ID NO 4
<211> LENGTH: 60
<212> TYPE: DNA
<213> ORGANISM: Artificial Sequence
<220> FEATURE:
<221> NAME/KEY: misc_feature
<222> LOCATION: (1)..(60)
<223> OTHER INFORMATION: primer 249

<400> SEQUENCE: 4
caatgggact gtcggaggac tgagggccaa agcttggctc ttagcctggg tcagggcatg    60

<210> SEQ ID NO 5
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: primer 247

<400> SEQUENCE: 5
ccgtcaccga gatctgatct cacgcg                                         26

<210> SEQ ID NO 6
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: primer 250

<400> SEQUENCE: 6
gcactgaggg ccaaagcttg gctc                                           24

<210> SEQ ID NO 7
<211> LENGTH: 25
<212> TYPE: DNA
<213> ORGANISM: Artificial Sequence
<220> FEATURE:
<221> NAME/KEY: misc_feature
<222> LOCATION: (1)..(25)
<223> OTHER INFORMATION: primer 251

<400> SEQUENCE: 7 ggatccccg atgagctaag ctagc                                           25

<210> SEQ ID NO 8
<211> LENGTH: 21
<212> TYPE: DNA
<213> ORGANISM: Artificial Sequence
<220> FEATURE:
<221> NAME/KEY: misc_feature
<222> LOCATION: (1)..(21)

```
<223> OTHER INFORMATION: primer 254

<400> SEQUENCE: 8
cttagcctgg gtcagggcat g                                              21

<210> SEQ ID NO 9
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: primer 258

<400> SEQUENCE: 9
ctacggcaat gtaccagctg                                                20

<210> SEQ ID NO 10
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: primer SP6

<400> SEQUENCE: 10
taatacgact cactataggg cga                                            23

<210> SEQ ID NO 11
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: primer T7

<400> SEQUENCE: 11
tttaggtgac actatagaat ac                                             22

<210> SEQ ID NO 12
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: primer 201(BNA01)

<400> SEQUENCE: 12
gcttggacta taatacctga c                                              21

<210> SEQ ID NO 13
<211> LENGTH: 953
<212> TYPE: DNA
<213> ORGANISM: Brassica napus
<220> FEATURE:
<221> NAME/KEY: misc_feature
<222> LOCATION: (1)..(953)
<223> OTHER INFORMATION: "n" can be any nucleotide a,c or g
      sequence comprising the 5' flanking region of MS-BN1

<400> SEQUENCE: 13
cccngccgcc atggccgcgg gattcttagc ctgggtcagg gcatgcatgg tgtgatccaa    60
agactttctc ggcccaaata ctaatcatca caagtcatgc atgatctgct cgggatggcc   120
```

```
aagaaaaatc gaacccatga caatattcac agttgtaagt ttttaccag tagacaaata      180 ccacttggtt taacatattg taaacttaat atatagaaga tgttcctatt cagaaaataa      240
tatatgtata tatataaaat tttattggcg actcgaggat gcacagaaat ataaaatgtt      300
ggtcgcttag accatctcca atgtatttct ctatttttac ctctaaaata aaggagctct      360
ataatagagg tgggttttgc tccaatgtat ttctttaaaa tagagatctc tacatataga      420
gcaaaatata gaggaatgtt atttcttcct ctataaatag aggagaaaat agcaatctct      480
attttagagg caaaaataga gatbsgttgg agtgattttg cctctaaatg ctattataga      540
ggtagaaata gaggtgggtt ggagatgctc ttactatttt catagtaggt gaaaacttga      600
aactagaaag ctttggagtg tacgagtgga aaacctctct ttgtagaaac atacacatgc      660
catttagtta actagttgac atagattttt gagtcagata actttaagaa tatatatgtt      720
tggatgagag tttgacactt tgagccactc gaaggacaaa ttttaaaaac ttgtgggatg      780
ctgtggccat aaaccttgag gacvsttttga tcatattcta ttaactacag tacgaatatg      840
attcgacctt tgcaattttc tcttcaggta ctcggccgtc gaactcggcc gtcgagtaca      900
tggtcgataa gaaaaggcaa tttgtagatg ttaattccca tcttgaaaga aat            953
```

<210> SEQ ID NO 14
<211> LENGTH: 16
<212> TYPE: DNA
<213> ORGANISM: Artificial Sequence
<220> FEATURE:
<221> NAME/KEY: misc_feature
<222> LOCATION: (1)..(14)
<223> OTHER INFORMATION: "n" stands for any nucleotide
      "s" stands for either nucleotide g or c
      "w" stands for nucleotide a or t/u. primer 611
<221> NAME/KEY: variation
<222> LOCATION: (1)..(11)
<223> OTHER INFORMATION: "n" stands for any nucleotide
      "s" stands for either nucleotide g or c
      "w" stands for nucleotide a or t/u

<400> SEQUENCE: 14
ngtcgaswgt ntwcaa                                                      16

<210> SEQ ID NO 15
<211> LENGTH: 22
<212> TYPE: DNA
<213> ORGANISM: Artificial Sequence
<220> FEATURE:
<221> NAME/KEY: misc_feature
<222> LOCATION: (1)..(15)
<223> OTHER INFORMATION: primer 259

<400> SEQUENCE: 15
gtgcagggaa gcggttaact gg                                               22

<210> SEQ ID NO 16
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: primer 260

<400> SEQUENCE: 16
cctttggagt aaatggtgtt gg                                               22

<210> SEQ ID NO 17

```
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: primer 24

<400> SEQUENCE: 17
gcgaatgtat attatatgca                                              20

<210> SEQ ID NO 18
<211> LENGTH: 537
<212> TYPE: DNA
<213> ORGANISM: Brassica napus
<220> FEATURE:
<221> NAME/KEY: misc_feature
<222> LOCATION: (1)..(537)
<223> OTHER INFORMATION: "n" stands for any nucleotide
      "s" stands for either nucleotide g or c
      "w" stands for nucleotide a or t/u
      sequence comprising the 3' flanking region of MS-BN1

<400> SEQUENCE: 18
gcgaatgtat attatatgca taatttatat attaaatgtg tataatcatg tataatcaat    60
gtataatcta tgtatatggt tagaaaaagt aaacaattaa tatagccggc tatttgtgta   120
aaaatcccta atataatcga cggatccccg ggaattccgg gggaagctta gatccatgga   180
tttgttatga taaccaaaaa caccctcctt tttattataa aggtagggat agctaatctg   240
ttattcggtt ttgattagag atattaatcc cgttttatca agtacagttt gatgtatttt   300
tttgttcgtt ttcattacaa tccaagacaa gttaggttta ttcattttta ccaaaaaaaa   360
aggtttggtt tattgtgaac attgctgcgg tttatttaaa tttgattcta ttcaaaggtc   420
aatccgtatt taacaagtaa actagtcttt atataatctt aaatctaacg atctttgatt   480
tttaaattgc atttanctat gtcctctctg gcgtatatgg tctctttgaa aacactc     537

<210> SEQ ID NO 19
<211> LENGTH: 19
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: primer 193

<400> SEQUENCE: 19
tgacactttg agccactcg                                               19

<210> SEQ ID NO 20
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: primer 48

<400> SEQUENCE: 20
ggagggtgtt tttggttatc                                              20

<210> SEQ ID NO 21
<211> LENGTH: 178
<212> TYPE: DNA
<213> ORGANISM: Brassica napus
<220> FEATURE:
```

```
<221> NAME/KEY: misc_feature
<222> LOCATION: (1)..(178)
<223> OTHER INFORMATION: sequence comprising the target site deletion of
      MS-BN1

<400> SEQUENCE: 21
gacactttga gccactcgaa ggacaaattt taaaaacttg tgggatgctg tggccataaa    60
ccttgaggac gctttgatca tattctatta actacagtac gaatatgatt cgacctttgc   120
aattttctct tgttttctaa ttcatatgga tttgttatga taaccaaaaa caccctcc     178

<210> SEQ ID NO 22
<211> LENGTH: 1198
<212> TYPE: DNA
<213> ORGANISM: Artificial Sequence
<220> FEATURE:
<221> NAME/KEY: misc_feature
<222> LOCATION: (1)..(1198)
<223> OTHER INFORMATION: insertion region of MS-BN1

<400> SEQUENCE: 22
catggtgtga tccaaagact ttctcggccc aaatactaat catcacaagt catgcatgat    60
ctgctcggga tggccaagaa aaatcgaacc catgacaata ttcacagttg taagtttttt   120
accagtagac aaataccact tggtttaaca tattgtaaac ttaatatata gaagatgttc   180
ctattcagaa aataatatat gtatatatat aaaattttat tggcgactcg aggatgcaca   240
gaaatataaa atgttggtcg cttagaccat ctccaatgta tttctctatt tttacctcta   300
aaataaagga gctctataat agaggtgggt tttgctccaa tgtatttctt taaaatagag   360
atctctacat atagagcaaa atatagagga atgttatttc ttcctctata aatagaggag   420
aaaatagcaa tctctatttt agaggcaaaa atagagatbs gttggagtga ttttgcctct   480
aaatgctatt atagaggtag aaatagaggt gggttggaga tgctcttact attttcatag   540
taggtgaaaa cttgaaacta gaaagctttg gagtgtacga gtggaaaacc tctctttgta   600
gaaacataca catgccattt agttaactag ttgacataga tttttgagtc agataacttt   660
aagaatatat atgtttggat gagagtttga cactttgagc cactcgaagg acaaatttta   720
aaaacttgtg ggatgctgtg gccataaacc ttgaggacvs tttgatcata ttctattaac   780
tacagtacga atatgattcg acctttgcaa ttttctcttc aggttttcta attcatatgg   840
atttgttatg ataaccaaaa acaccctcct ttttattata aagtagggga tagctaatct   900
gttattcggt tttgattaga gatattaatc ccgttttatc aagtacagtt tgatgtattt   960
ttttgttcgt tttcattaca atccaagaca agttaggttt attacatttt accaaaaaaa  1020
aaggtttggt ttattgtgaa cattgctgcg gttttatttaa atttgattct attcaaaggt  1080
caatccgtat ttaacaagta aactagtctt tatataatct taaatctaac gatctttgat  1140
ttttaaattg catttancta tgtcctctct ggcgtatatg gtctctttga aaacactc    1198

<210> SEQ ID NO 23
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: primer 193 (BN03)

<400> SEQUENCE: 23
tcatctacgg caatgtacca gc                                              22
```

<210> SEQ ID NO 24
<211> LENGTH: 1077
<212> TYPE: DNA
<213> ORGANISM: Brassica napus
<220> FEATURE:
<221> NAME/KEY: misc_feature
<222> LOCATION: (1)..(1077)
<223> OTHER INFORMATION: sequence comprising the 5' flanking region of
      MS-BN1

<400> SEQUENCE: 24
gagctctccc atatggtcga cctgcaggcg gccgcactag tgattcttag cctgggtcag      60
ggcatggcat gtctgatggt acatgctaaa tgctatattt cctgttttaa gtgttaaaat     120
cattttctga tggaactaaa tccagtttta agagtaactg acaagtacaa ttaagcacaa     180
caatataata gtagtaattg gcatctttga ttgttaaata tcaaaacagt aaagttacaa     240
aaaaaaatac caaaccaata atgaagactt ggcggagaca gtgccgtgcg aaggttttcg     300
gaggtccgag acgagttcaa aaatacattt tacataatat attttttcata tatatatata     360 tataacattc aaaagtttga attattacat aaacgttttc taaattttct tcaccaaaat     420
tttataaact aaattttaa atcatgaaca aaaagtatga atttgtaata taaatacaaa     480
gatacaaatt tttgattgaa atattggtag ctgtcaaaaa agtaaatctt agaatttaaa     540
ttaactatag taaactatat attgaaaata ttataaattt ttatcaaatt ctcataaata     600
tataaaataa atctaactca tagcatataa aagaagact aatgtggatc aaaatatttta    660 cagtttttta gaagtagaat ctttatagtt ttatttaaaa tatagcaaaa atgatcacaa     720
acctagttay ttaaggagaa gtccaattca aaatcaaata aaaataaaat ctatctaaaa     780
aaatatgtta actaccatgc aaaagtattt tttttgtaat tagaaaccct gaaatttgta     840
caaaacttgg acccctaggt aaatgccttt ttcatctcgc gataagaaaa ggcaatttgt     900
agatgttaat tcccatcttg aaagaaatat agtttaaata tttattgata aaataacaag     960
tcaggtatta tagtccaagc aaaaacataa atttattgat gcaagtttaa attcagaaat    1020
atttcaataa ctgattatat cagctggtac atcgccgtag aatcccgcgc catggcg       1077

<210> SEQ ID NO 25
<211> LENGTH: 16
<212> TYPE: DNA
<213> ORGANISM: Artificial Sequence
<220> FEATURE:
<221> NAME/KEY: misc_feature
<222> LOCATION: (1)..(16)
<223> OTHER INFORMATION: "n" stands for any nucleic acid
      "s" stands for G or C
      "w" stands for A or T/U
      primer 314

<400> SEQUENCE: 25
ntgcgaswga nawgaa                                                      16

<210> SEQ ID NO 26
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: primer 314

<400> SEQUENCE: 26
gtaggaggtt gggaagacc                                                   19

<210> SEQ ID NO 27
<211> LENGTH: 25
<212> TYPE: DNA
<213> ORGANISM: Artificial Sequence
<220> FEATURE:
<221> NAME/KEY: misc_feature
<222> LOCATION: (1)..(25)
<223> OTHER INFORMATION: primer 315

<400> SEQUENCE: 27
gggctttcta ctagaaagct ctcgg                                   25

<210> SEQ ID NO 28
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: primer 316

<400> SEQUENCE: 28
ccgataggga agtgatgtag gagg                                    24

<210> SEQ ID NO 29
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: primer 288

<400> SEQUENCE: 29
atgcagcaag aagcttggag g                                       21

<210> SEQ ID NO 30
<211> LENGTH: 1501
<212> TYPE: DNA
<213> ORGANISM: Brassica napus
<220> FEATURE:
<221> NAME/KEY: misc_feature
<222> LOCATION: (1)..(1501)
<223> OTHER INFORMATION: "n" stands for any nucleotide
      "s" stands for either nucleotide g or c
      "w" stands for nucleotide a or t/u
      sequence comprising the 3' flanking region of RF-BN1.

<400> SEQUENCE: 30
ccatggccgc gggattgtag gaggttggga agacaggccc agaaagagat ttatctgact    60
cgttttgtgt atagttttca atgttcataa aggaagatgg agacttgaga agttttttttt   120 ggactttgtt tagctttgtt gggcgttttt ttttttttgat caataacttt gttgggctta   180
tggtcgataa gcgtgcgcat gtctgatggt acatgctaaa tgctatattt ctgtttaaag    240
tgttaaaatc attttctgat ggaactaaat ccagttttaa gagtaactga caagtacaat    300
taagcacaac ataaaatag  tagtaattgg catctttgat tgttaaatat caaaacaata    360
aagttacaaa aaaaatacc  aaaccaataa tgaagacttg gcggagacag tgccgtgcga    420
aggttttcgg aggtccgaga cgagttcaaa atacatttt acataatata tttttcatat     480
atatatatat ataaacatt caaagtttg aattattaca taaacgtttt ctaaattttc      540
ttcaccaaaa ttttataaac taaaatttt maatcatgaa caaaaagtat gaatttgtaa     600 tataaataacm aagatacaaa ttttttgattg aaatattggt agctgtcaaa aaagtaaatc  660

-continued

```
ttagaattta aattaactat agtaaactat atatggaaaa tattataaat ttttatcaaa      720
ttctcataaa tatataaaat aaatctaact catagcatat aaaaagaaga ctaatgtgga      780
tcaaratatt tacagttttt tagaagtaga atctctatag ttttatttaa aatatagcaa      840
aaatgatcac aaacctagtt actttaacca gaagtccaat tcaaaatcaa ataaaaataa      900
aaatctatct aaaaaaatat gttaactacc atgcaaaagt attttttttt gtaattagaa      960
accctgaaat ttgtacaaaa cttggacccc taggtaaatt ccctagaaag tatcctatta     1020
gcgtcgacaa actgttgctc atattttct ctccttactt tatatcatac actaatatan     1080
gnagatgatc taattaatta ttcatttcca tgctagctaa ttcaagaaaa agaaaaaaaa     1140
ctattatcta aacttatatt cgagcaacac ctcggagata acaggatata tgtcattaat     1200
gaatgcttga actcatctcg cgaactcatc tcgcatcgct tatagccaca aagatccaac     1260
ccctctcttc aatcatatat cagtagtaca atacaaatag atattgtgag cacatatgcc     1320
gtctagtact gatgtgtaca tgtagaggag ccgcaaatgt ttagtcactc caacaaatga     1380
gcatgaccac gcatcttctg atgatgtaca gccgtccctt ttgctctctc aaatatcctc     1440
caagcttctt gctgcataaa tcactagtgc ggccgcctgc aggtcgacca tatgggagag     1500
c                                                                    1501
```

<210> SEQ ID NO 31
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: primer 269

<400> SEQUENCE: 31
ggttttcgga ggtccgagac g                                                21

<210> SEQ ID NO 32
<211> LENGTH: 21
<212> TYPE: DNA
<213> ORGANISM: Artificial Sequence
<220> FEATURE:
<221> NAME/KEY: misc_feature
<222> LOCATION: (1)..(283)
<223> OTHER INFORMATION: primer 283

<400> SEQUENCE: 32
cttggacccc taggtaaatg c                                                21

<210> SEQ ID NO 33
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: primer 284

<400> SEQUENCE: 33
gtacaaaact tggacccta gg                                                22

<210> SEQ ID NO 34
<211> LENGTH: 1068
<212> TYPE: DNA
<213> ORGANISM: Brassica napus
<220> FEATURE:

<210> SEQ ID NO 35
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: primer 57

```
<221> NAME/KEY: misc_feature
<222> LOCATION: (1)..(1068)
<223> OTHER INFORMATION: "n" stands for any nucleotide
      "s" stands for either nucleotide g or c
      "w" stands for nucleotide a or t/u
      integration region of RF-BN1.

<400> SEQUENCE: 34
cgcgttggga gctctcccat atggtcgacc tgcaggcggc cgcactagtg attcttggac    60
ccctaggtaa atgccttttt caaaagcctc taagcacggt tctgggcggg gagtcagcga   120
gaaaaaaga tatttcccta gaaagtatcc tattagcgtc gacaaactgt tgctcatatt   180
tttctctcct tactttatat catacactaa tataaaaaga tgatctaatt aattattcat   240
ttccatgcta gctaattcaa gaaaagaaa aaaactatta tctaaactta tattcgagca   300
acacctcgga gataacagga tatatgttat taatgaatgc ttgaactcat ctcgcgaact   360
catctcgcat cgcttatagc cacaaagatc caacccctct cttcaatcat atatcagtag   420
tacaatacaa atagatattg tgagcacata tgccgtctag tactgatgtg tatatgtaga   480
gganngcaaa tgtttagtca ctccaacaaa tgagcatgac nacgcatctt ctgatgatgt   540
acagccgtcc cttttgctct ctcaaatatc ctccaagctt cttgctgcat ggaatcttct   600
tcttggtgtc tttcatgata acaaaatcta acgagagaga aacccttagt caagaaaaaa   660
caaataaaac tctaacgaga gtgtgtgaga agtagagag tatgtgtgag tgacggagag   720
aaagtgagac cataaagatg ttgtgcaaag agagcaagac ttaacctata tatactcaca   780
tacacgtaca catcataccc attanagata ataaaaagga aaaaggaaca actaacaagg   840
gaactgtatc ccatacttta tctcatcata catgatgcat aatatattct ttcgtatatc   900
aagaaaatg agcctgatat ttttttattt cgaaactaaa agagtgtcta tttctctctc   960
ttagagatag tgccatgtca aatttctaag aagtagcaag atttacaaag gaatctaaag   1020
caaccccacg cgcattgtgt tcatttctct cgaccatccc gcggccat                  1068
```

<400> SEQUENCE: 35

```
gcatgatctg ctcgggatgg c                                              21
```

<210> SEQ ID NO 36
<211> LENGTH: 909
<212> TYPE: DNA
<213> ORGANISM: Artificail sequence
<220> FEATURE:
<221> NAME/KEY: misc_feature
<222> LOCATION: (1)..(909)
<223> OTHER INFORMATION: sequence comprising the 5' flanking region of
      MS-BN1 in WOSR

<400> SEQUENCE: 36

```
tgcatgatct gctcgggatg gccaagaaaa atcgaaccca tgacaatatt cacagttgta    60
agttttttac cagtagacaa ataccacttg gttaacata ttgtaaactt aatatataga    120
agatgttcct attcagaaaa taatatatgt atatatataa aattttattg gcgactcgag    180
gatgcacaga aatataaaat gttggtcgct tagaccatct ccaatgtatt tctctatttt   240
```

```
tacctctaaa ataaggaac tctataatag aggtgggttt tactccaatg tatttcttta      300
aaatagagat ctctacatat agagcaaaat atagaggaat gttatttctt cctctataaa     360
tagaggagaa aatagcaatc tctattttag aggcaaaaat agagatgggt tggagtgatt     420
ttgcctctaa atgctattat agaggtagaa atagaggtgg gttggagatg ctcttactat     480
tttcatagta ggtgaaaact tgaaactaga agctttgga gtgtacgagt ggaaaacctc      540
tctttgtaga aacatacaca tgccatttag ttaactagtt gacatagatt tttgagtcag    600
ataactttaa gaatatatat gtttggatga gagtttgaca ctttgagcca ctcgaaggac    660 aaatttttaaa aacttgtggg atgctgtggc ccataaacct tgaggacgct ttgatcatat   720
tctattaact acagtacgaa tatgattcga cctttgcaat tttctcttca gtactcggcc    780
gtcgaactcg gccgtcgagt acatggtcga taagaaaagg caatttgtag atgttaattc    840
ccatcttgaa agaaatatag tttaaatatt tattggataa ataacaagt caggtattat     900 agtccaagc                                                             909

<210> SEQ ID NO 37
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: primer 68

<400> SEQUENCE: 37
ccatatacgc cagagaggac                                                 20

<210> SEQ ID NO 38
<211> LENGTH: 522
<212> TYPE: DNA
<213> ORGANISM: Brassica napus
<220> FEATURE:
<221> NAME/KEY: misc_feature
<222> LOCATION: (1)..(522)
<223> OTHER INFORMATION: sequence comprising the 3' flanking region of
      MS-BN1 in WOSR

<400> SEQUENCE: 38
gcgaatgtat attatatgca taatttatat attaaatgtg tataatcatg tataatcaat    60
gtataatcta tgtatatggt tagaaaaagt aaacaattaa tatagccggc tatttgtgta    120
aaaatcccta atataatcga cggatccccg ggaattccgg gggaagctta gatccatgga   180
tttgttatga taaccaaaaa caccctcctt tttattataa aggtagggat agctaatctg   240
ttattcggtt ttgattagag atattaatcc cgttttatca agtacagttt gatgtatttt   300
tttgttcgtt ttcattacaa tccaagacaa gttaggttta ttacatttta ccaaaaaaaa   360
aggtttggtt tattgtgaac attgctgcgg ttttatttaa atttgattct attcaaaggt   420
caatccgtat ttaacaagta aactagtctt tatataatct taaatctaac gatacttgga   480
tttttaaatt gcatttagct atgtcctctc tggcgtatat gg                     522

<210> SEQ ID NO 39
<211> LENGTH: 694
<212> TYPE: DNA
<213> ORGANISM: Brassica napus
<220> FEATURE:
<221> NAME/KEY: misc_feature
<222> LOCATION: (1)..(694)
<223> OTHER INFORMATION: sequence comprising the 5' flanking region of
```

RF-BN1 in WOSR

<400> SEQUENCE: 39

```
ggttttcgga ggtccgagac gagttcaaaa atacatttta cataatatat ttttcatata    60
tatatatata tataacattc aaaagtttga attattacat aaacgttttc taaattttct   120
tcaccaaaat tttataaact aaaattttta aatcatgaac aaaaagtatg aatttgtaat   180
ataaatacaa agatacaaat ttttgattga atatattggta gctgtcaaaa aagtaaatct   240
tagaatttaa attaactata gtaaactata tattgaaaat attataaatt tttatcaaat   300
tctcataaat atataaaata aatctaactc atagcatata aaaagaagac taatgtggat   360
caaaatattt acagttttt agaagtagaa tctttatagt tttatttaaa atatagcaaa   420
aatgatcaca aacctagtta ctttaaccag aagtccaatt caaaatcaaa taaaaataaa   480
aatctatcta aaaaatatg ttaactacca tgcaaaagta ttttttttg taattagaaa   540
ccctgaaatt tgtacaaaac ttggacccct aggtaaatgc cttttcatc tcgcgataag   600
aaaaggcaat ttgtagatgt taattcccat cttgaaagaa atatagttta aatatttatt   660
gataaaataa caagtcaggt attatagtcc aagc                              694
```

<210> SEQ ID NO 40
<211> LENGTH: 1279
<212> TYPE: DNA
<213> ORGANISM: Brassica napus
<220> FEATURE:
<221> NAME/KEY: misc_feature
<222> LOCATION: (1)..(1279)
<223> OTHER INFORMATION: sequence comprising the 3' flanking region of RF-BN1 in WOSR

<400> SEQUENCE: 40

```
ggggtttt ttttttgatc aataactttg ttgggcttat ggtcgataag cgtgcgcatg    60
tctgatggta catgctaaat gctatatttc tgtttaaagt gttaaaatca ttttctgatg   120
gaactaaatc cagttttaag agtaactgac aagtacaatt aagcacaaca ataaaatagt   180
agtaattggc atctttgatt gttaaatatc aaacaataaa gttcaaaaaa aaataccaac   240
ccaataatga agacttggcg gagacagtgc cgtgcgaagg ttttcggagg tccgagacga   300
gttcaaaaat acatttaca taatatattt ttcatatata tatatatata taacattcaa   360
aagtttgaat tattacataa acgttttcta aattttcttc accaaaattt tataaactaa   420
aattttaaa tcatgaacaa aaagtatgaa tttgtaatat aaatacaaag atacaaattt   480
ttgattgaaa tattggtagc tgtcaaaaaa gtaaatctta gaatttaaat taactatagt   540
aaactatata ttgaaaatat tataaatttt tatcaaattc tcataaatat ataaataaa   600
tctaactcat agcatataaa aagaagacta atgtggatca aaatatttac agttttttag   660
aagtagaatc tttatagttt tatttaaaat atagcaaaaa tgatcacaaa cctagttact   720
ttaaccagaa gtccaattca aaatcaaata aaaataaaaa tctatctaaa aaaatatgtt   780
aactaccatg caaagtatt ttttttgta attagaaacc ctgaaattg tacaaaactt   840
ggacccctag gtaaattccc tagaagtat cctattagcg tcgacaaact gttgctcata   900
tttttctctc cttactttat atcatacact aatataaaa gatgatctaa ttaattattc   960
atttccatgc tagctaattc aagaaaaaga aaaaaaactt attatctaaa cttatattcg  1020
agcaacacct cggagataac aggatatatg tcattaatga atgcttgaac tcatctcgcg  1080
aactcatctc gcatcgctta tagccacaaa gatccaaccc ctctcttcaa tcatatatca  1140
```

```
gtagtacaat acaaatagat attgtgagca catatgccgt ctagtactga tgtgtatatg      1200
tagaggagcc gcaaatgttt agtcactcca acaaatgagc atgaccacgc atcttctgat      1260
gatgtacagc cgtcccttt                                                   1279

<210> SEQ ID NO 41
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: primer 268 ( BNA 04)

<400> SEQUENCE: 41
tggaccccta ggtaaatgcc                                                    20

<210> SEQ ID NO 42
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: prmer BNA05

<400> SEQUENCE: 42
aacgagtgtc agctagacca gc                                                 22

<210> SEQ ID NO 43
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: primer BNA06

<400> SEQUENCE: 43
cgcagttctg tgaacatcga cc                                                 22
```